US008295914B2

(12) United States Patent
Kalafut et al.

(10) Patent No.: US 8,295,914 B2
(45) Date of Patent: Oct. 23, 2012

(54) SYSTEMS AND METHODS OF DETERMINING PATIENT TRANSFER FUNCTIONS AND MODELING PATIENT RESPONSE TO A PHARMACEUTICAL INJECTION

(75) Inventors: John F. Kalafut, Oakmont, PA (US); Arthur E. Uber, III, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 1297 days.

(21) Appl. No.: 11/575,846

(22) PCT Filed: Nov. 16, 2005

(86) PCT No.: PCT/US2005/041913
§ 371 (c)(1),
(2), (4) Date: Mar. 22, 2007

(87) PCT Pub. No.: WO2006/055813
PCT Pub. Date: May 26, 2006

(65) Prior Publication Data

US 2008/0097197 A1 Apr. 24, 2008

Related U.S. Application Data

(60) Provisional application No. 60/628,201, filed on Nov. 16, 2004.

(51) Int. Cl.
*A61B 6/00* (2006.01)

(52) U.S. Cl. ...................................................... 600/431

(58) Field of Classification Search .............. 604/65–67, 604/131, 30, 246; 600/431–435
See application file for complete search history.

(56) References Cited

U.S. PATENT DOCUMENTS 3,701,345 A 10/1972 Heilman et al.

(Continued)

FOREIGN PATENT DOCUMENTS

CA 2045070 A1 2/1992

(Continued)

OTHER PUBLICATIONS

Cademartiri, F and Luccichenti, G., et al. (2004) "Sixteen-Row Multislice Computed Tomography:Basic Concepts, Protocols, and Enhanced Clinical Application," Semin Ultrasound CT MR 25(1):2-16.

(Continued)

*Primary Examiner* — Manuel Mendez

(74) *Attorney, Agent, or Firm* — James R. Stevenson; Gregory L. Bradley; Henry E. Bartony, Jr.

(57) ABSTRACT

A method of controlling an injector system for delivering a contrast enhancing fluid to a patient. The method includes the step of determining at least one patient transfer function for the patient based upon data specific to the patient, with the at least one patient transfer function providing a time enhancement output for a given input. The data specific to the patent may include at least one of an estimate of physiologic parameters of the patient, an estimate of anatomic parameters of the patient and an enhancement caused by an injection of the contrast enhancing fluid into the patient. Other steps involve: determining a desired time enhancement output; using the at least one patient transfer function to determine an injection procedure input; and controlling the injector system at least in part on the basis of the determined injection procedure input.

58 Claims, 17 Drawing Sheets

U.S. PATENT DOCUMENTS 3,812,843 A 5/1974 Wootten et al.
3,888,239 A 6/1975 Rubinstein
3,898,983 A 8/1975 Elam
3,941,126 A 3/1976 Dietrich et al.
4,090,502 A 5/1978 Tajika
4,135,247 A 1/1979 Gordon et al.
4,151,845 A 5/1979 Clemens
4,187,057 A 2/1980 Xanthopoulos
4,191,183 A 3/1980 Mendelson
4,207,871 A 6/1980 Jenkins
4,280,494 A 7/1981 Cosgrove, Jr. et al.
4,319,568 A 3/1982 Tregoning
4,340,153 A 7/1982 Spivey
4,392,849 A 7/1983 Petre et al.
4,396,385 A 8/1983 Kelly et al.
4,402,310 A 9/1983 Kimura
4,409,966 A 10/1983 Lambrecht et al.
4,444,198 A 4/1984 Petre
4,447,230 A 5/1984 Gula et al.
4,477,923 A 10/1984 Baumann et al.
4,479,761 A 10/1984 Bilstad et al.
4,512,764 A 4/1985 Wunsch
4,544,949 A 10/1985 Kurihara
4,551,133 A 11/1985 Zegers de Beyl et al.
4,559,036 A 12/1985 Wunsch
4,563,175 A 1/1986 LaFond
4,585,009 A 4/1986 Barker et al.
4,611,340 A 9/1986 Okazaki
4,633,307 A 12/1986 Honda
4,634,426 A 1/1987 Kamen
4,636,144 A 1/1987 Abe et al.
4,655,197 A 4/1987 Atkinson
4,672,651 A 6/1987 Horiba et al.
4,710,166 A 12/1987 Thompson et al.
4,723,261 A 2/1988 Janssen et al.
4,750,643 A 6/1988 Wortrich
4,754,786 A 7/1988 Roberts
4,783,273 A 11/1988 Knutsson et al.
4,795,429 A 1/1989 Feldstein
4,798,590 A 1/1989 O'Leary et al.
4,838,856 A 6/1989 Mulreany et al.
4,840,620 A 6/1989 Kobayashi et al.
4,853,521 A 8/1989 Claeys et al.
4,854,324 A 8/1989 Hirschman et al.
4,857,056 A 8/1989 Talonn
4,874,359 A 10/1989 White et al.
4,880,014 A 11/1989 Zarowitz et al.
4,887,554 A 12/1989 Whitford
4,903,705 A 2/1990 Imamura et al.
4,913,154 A 4/1990 Ermert et al.
4,925,444 A 5/1990 Orkin et al.
4,943,279 A 7/1990 Samiotes et al.
4,946,439 A 8/1990 Eggers
4,966,579 A 10/1990 Polaschegg
4,995,064 A * 2/1991 Wilson et al. .............. 378/98.12
5,009,654 A 4/1991 Minshall et al.
5,018,173 A 5/1991 Komai et al.
5,032,112 A 7/1991 Fairchild et al.
5,034,987 A 7/1991 Fujimoto et al.
5,040,537 A 8/1991 Katakura
5,078,683 A 1/1992 Sancoff et al.
5,088,981 A 2/1992 Howson et al.
5,104,374 A 4/1992 Bishko et al.
5,111,492 A 5/1992 Klausz
5,128,121 A 7/1992 Berg et al.
5,135,000 A 8/1992 Akselrod et al.
5,180,896 A 1/1993 Gibby et al.
5,267,174 A 11/1993 Kaufman et al.
5,300,031 A 4/1994 Neer et al.
5,301,672 A 4/1994 Kalender
5,310,997 A 5/1994 Roach et al.
5,317,506 A 5/1994 Coutre et al.
5,328,463 A 7/1994 Barton et al.
5,339,799 A 8/1994 Kami et al.
5,349,625 A 9/1994 Born et al.
5,361,761 A 11/1994 Van Lysel et al.
5,368,562 A 11/1994 Blomquist et al.
5,368,567 A 11/1994 Lee
5,378,231 A 1/1995 Johnson et al.
5,382,232 A 1/1995 Hague et al.
5,383,858 A 1/1995 Reilly et al.
5,385,540 A 1/1995 Abbott et al.
5,400,792 A 3/1995 Hoebel et al.
5,417,213 A 5/1995 Prince
5,431,627 A 7/1995 Pastrone et al.
5,445,621 A 8/1995 Poli et al.
5,456,255 A 10/1995 Abe et al.
5,458,128 A 10/1995 Polanyi et al.
5,459,769 A 10/1995 Brown
5,469,849 A 11/1995 Sasaki et al.
5,472,403 A 12/1995 Cornacchia et al.
5,474,683 A 12/1995 Bryant et al.
5,485,831 A 1/1996 Holdsworth et al.
5,494,036 A 2/1996 Uber, III et al.
5,494,822 A 2/1996 Sadri
5,496,273 A 3/1996 Pastrone et al.
5,507,412 A 4/1996 Ebert et al.
5,515,851 A 5/1996 Goldstein
5,522,798 A 6/1996 Johnson et al.
5,531,679 A 7/1996 Schulman et al.
5,569,181 A 10/1996 Heilman et al.
5,569,208 A 10/1996 Woelpper et al.
5,573,515 A 11/1996 Wilson et al.
5,583,902 A 12/1996 Bae
5,687,208 A 11/1997 Bae et al.
5,713,358 A 2/1998 Mistretta et al.
5,724,976 A 3/1998 Mine et al.
5,739,508 A 4/1998 Uber, III
5,743,266 A 4/1998 Levene et al.
5,768,405 A 6/1998 Makram-Ebeid
5,796,862 A 8/1998 Pawlicki et al.
5,840,026 A 11/1998 Uber, III et al.
5,865,744 A 2/1999 Lemelson
5,881,124 A 3/1999 Giger et al.
6,055,985 A 5/2000 Bae et al.
6,073,042 A 6/2000 Simonetti
6,201,889 B1 3/2001 Vannah
6,236,706 B1 5/2001 Hsieh
6,317,623 B1 11/2001 Griffiths et al.
6,344,030 B1 2/2002 Duchon et al.
6,385,483 B1 5/2002 Uber, III et al.
6,397,097 B1 5/2002 Requardt
6,397,098 B1 5/2002 Uber, III et al.
6,402,697 B1 6/2002 Calkins et al.
6,470,889 B1 * 10/2002 Bae et al. ........................ 604/28
6,471,674 B1 10/2002 Emig et al.
6,478,735 B1 11/2002 Pope et al.
6,556,695 B1 4/2003 Packer et al.
6,626,862 B1 9/2003 Duchon et al.
6,635,030 B1 10/2003 Bae et al.
6,643,537 B1 11/2003 Zatezalo et al.
6,652,489 B2 11/2003 Trocki et al.
6,656,157 B1 12/2003 Duchon et al.
6,673,033 B1 1/2004 Sciulli et al.
6,731,971 B2 5/2004 Evans, III et al.
6,776,764 B2 8/2004 Pinsky
6,876,720 B2 4/2005 Tsuyuki
6,901,283 B2 5/2005 Evans, III et al.
6,970,735 B2 11/2005 Uber, III et al.
7,094,216 B2 8/2006 Trombley, III et al.
7,326,186 B2 2/2008 Trombley, III et al.
2003/0135111 A1 7/2003 Meaney et al.
2003/0212364 A1 11/2003 Mann et al.
2003/0216683 A1 11/2003 Shekalim
2004/0008028 A1 1/2004 Horger et al.
2004/0010229 A1 1/2004 Houde et al.
2004/0025452 A1 2/2004 McLean
2004/0064040 A1 4/2004 Masuda et al.
2004/0097875 A1 5/2004 Bae
2004/0162484 A1 8/2004 Nemoto
2004/0215144 A1 10/2004 Duchon et al.

FOREIGN PATENT DOCUMENTS

DE 3726452 A1 2/1989
DE 4426387 A1 8/1995
EP 0189491 A1 8/1986
EP 0619122 A1 10/1994

| | | | |
|---|---|---|---|
| FR | 2493708 | A1 | 5/1982 |
| FR | 2561949 | A1 | 10/1985 |
| JP | 50017781 | A | 2/1975 |
| JP | 58015842 | A | 1/1983 |
| JP | 59214432 | A | 12/1984 |
| JP | 60194934 | A | 10/1985 |
| JP | 60194935 | A | 10/1985 |
| JP | 60253197 | A | 12/1985 |
| JP | 62216199 | A | 9/1987 |
| JP | 63290547 | A | 11/1988 |
| JP | 1207038 | A | 8/1989 |
| JP | 2224647 | A | 9/1990 |
| JP | 2234747 | A | 9/1990 |
| JP | 3055040 | A | 3/1991 |
| JP | 4115677 | A | 4/1992 |
| JP | 5084296 | A | 4/1993 |
| JP | 7178169 | A | 7/1995 |
| JP | 10211198 | A | 8/1998 |
| WO | 8500292 | A1 | 1/1985 |
| WO | 8803815 | A1 | 6/1988 |
| WO | 9415664 | A1 | 7/1994 |
| WO | 9820919 | A1 | 5/1998 |
| WO | 0061216 | A1 | 10/2000 |

OTHER PUBLICATIONS

D. Fleischmann and K. Hittmair, "Mathematical Analysis of Arterial Enhancement and Optimization of Bolus Geometry for CT Angiography Using the Discrete Fourier Transform," J Comput Assist Tomogr, vol. 23, pp. 474-84, 1999.

Guytan, A.C., "Circulatory Physiology: Cardiac Output and Regulation", Saunders, Philadelphia, p173, ISBN:07216436004.

Sablayrolles, J-L, "Cardiac CT: Experience from Daily Practice", Advance CT, A GE Healthcare Publication. Aug. 2004.

"Digital Injector for Angiography", Sias. (Sep. 7, 1993).

"Angiomat 6000 Digital Injection System—Operator's Manual", Rev. Jan. 1990.

Fleischmann, Dominik, "Present and Future Trends in Multiple Detector-Row CT Applications; CT Angiography", Eur. Radio!. 12 (Suppl. 2) 2002.

International Search Report and Written Opinion for counterpart PCT Application No.: PCT/US2005/41913.

Korosec, Frank, "Basic Principles of Phase-contrast, Time-of-flight, and Contrast-enhanced MR Angiography", 1999.

Cademartiri, F and Luccichenti, G., et al. (2004) "Sixteen-Row Multislice Computed Tomography:Basic Concepts, Protocols, and Enhanced Clinical Application," Semin Ultrasound CT MR 25(1):2-16, Date: 2004.

K.T. Bae, J.P. Heiken, and J.A. Brink, "Aortic and Hepatic Contrast Medium Enhancement at CT. Part I. Prediction and a Computer Model," Radiology, vol. 207, pp. 647-655, 1998.

K.T. Bae, "Peak Contrast Enhancement in CT and MR Angiography: When Does It Occur and Why? Pharmacokinetic Study in a Porcine Model," Radiology, vol. 227, pp. 809-816, 2003.

K.T. Bae et al., "Multiphasic Injection Method for Uniform Prolonged Vascular Enhancement at CT Angiography: Pharmacokinetic Analysis and Experimental Porcine Method," Radiology, vol. 216, pp. 872-880, 2000.

D. Fleischmann and K. Hittmair, "Mathematical Analysis of Arterial Enhancement and Optimization of Bolus Geometry for CT Angiography Using the Discrete Fourier Transform," J Comput Assist Tomogr, vol. 23, pp. 474-484, 1999.

Fisher and Teo, "Optimal Insulin Infusion Resulting from a Mathematical Model of Blood Glucose Dyanamics", IEEE Trans Biomed Eng, vol. 36(4), pp. 479-486, 1989.

Jacobs, "Algorithm for Optimal Linear Model-Based Control with Application to Pharmacokinetic Model-Driven Drug Delivery", IEEE Trans Biomed Eng, vol. 37(1), pp. 107-109, 1990.

Wada and Ward, "The Hybrid Model: A New Pharmacokinetic Model for Computer-Controlled Infusion Pumps", IEEE Trans. Biomed. Eng, vol. 41(2), pp. 134-142, 1994.

Wada and Ward, "Open Loop Control of Multiple Drug Effects in Anesthesia", IEEE Trans. Biomed Eng, vol. 42(7), pp. 666-677, 1995.

Neatpisarnvanit and Boston, "Estimation of Plasma Insulin from Plasma Glucose", IEEE Trans Biomed Eng, vol. 49 (11), pp. 1253-1259, 2002.

Gentilini et al., "A New Paradigm for the Closed-Loop Intraoperative Administration of Analgesics in Humans", IEEE Tran Biomed Eng, vol. 49(4), pp. 289-2999, 2002.

Guytan, A.C., "Circulatory Physiology: Cardiac Output and Regulation", Saunders, Philadelphia, p173, ISBN:07216436004, Date: 1985.

Mahnken, A.H., Henzler, D, et al., "Determination of Cardiac Output with Multislice Spiral Computed Tomography: A Validation Study", Invest Radiol 39(8): 451-4, 2004.

Mahnken, A.H., Klotz, E., et al., "Measurement of Cardiac Output from a Test-Bolus Injection in Multislice Computed Tomography", Eur Radiol 13(11): 2498-504, 2003.

Garrett, J.S., Lanzer, P., et al., "Measurement of Cardiac Output by Cine Computed Tomography", Am J Cardiol 56 (10): 657-61, 1985.

* cited by examiner

Fig. 2C
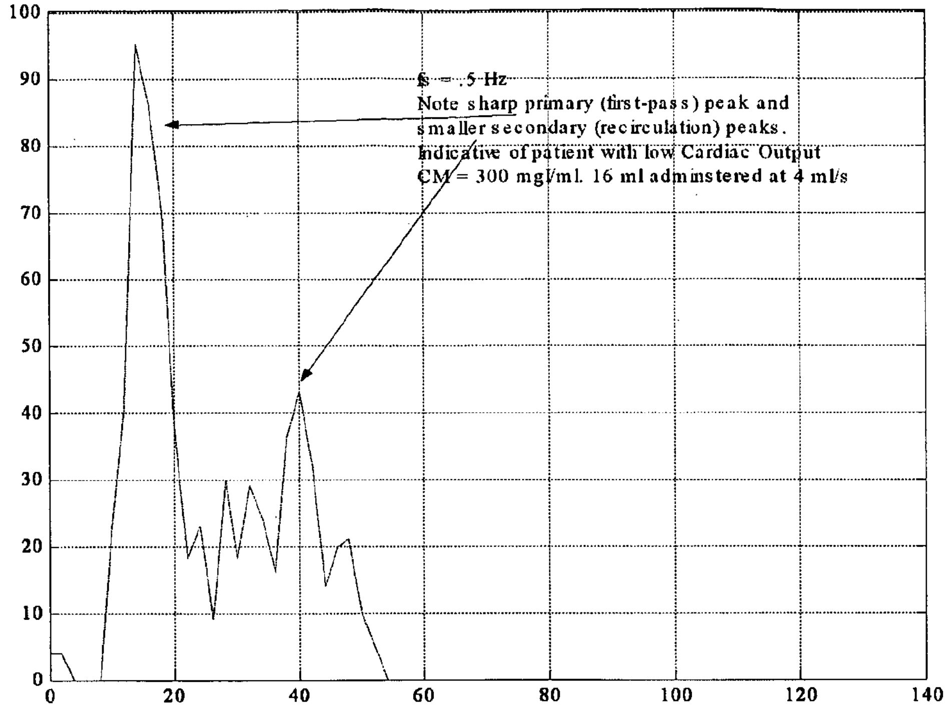
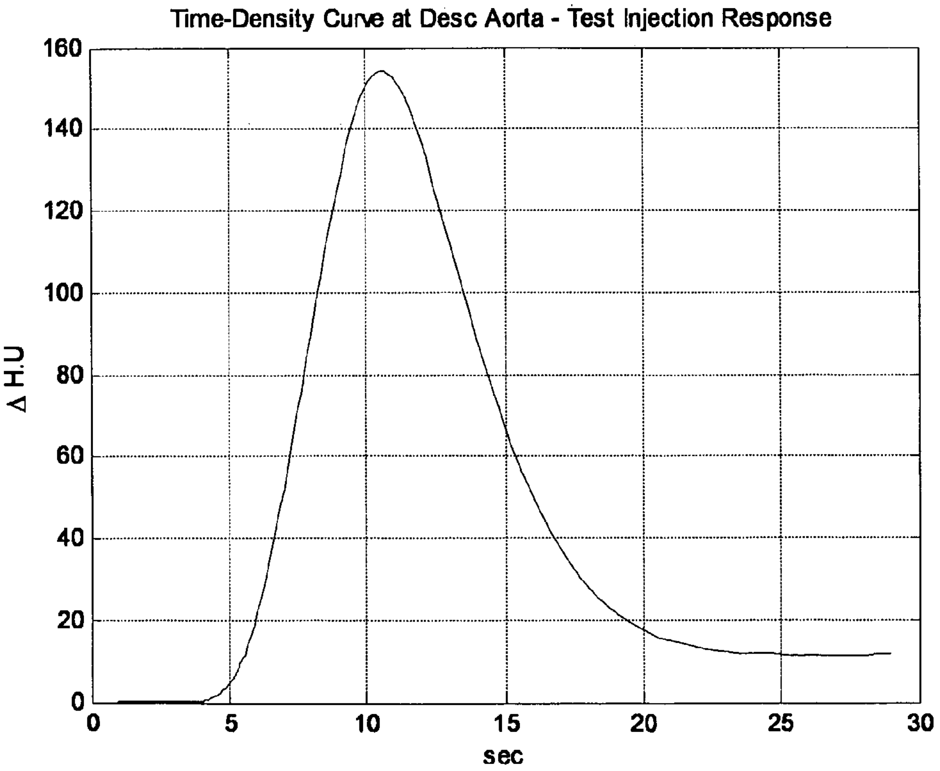
Fig. 2A

P1- Relative Test Enhancement w/ saline in AA
Relative test enh-SD
Relative test enh
Relative test enh + SD Relative test enh - SD
Relative test enh
Relative test enh + SD
0
50
100
150
200
250
300
350
400
450
500
0 5 10 15 20 25 30 35 40 45 50

P2- Relative Test Enhancement w/ saline in AA
Relative test enh-SD
Relative test enh
Relative test enh + SD Relative test enh - SD
Relative test enh
Relative test enh + SD
0
50
100
150
200
250
300
350
400
450
500
0 5 10 15 20 25 30 35 40 45 50

Fig. 18A
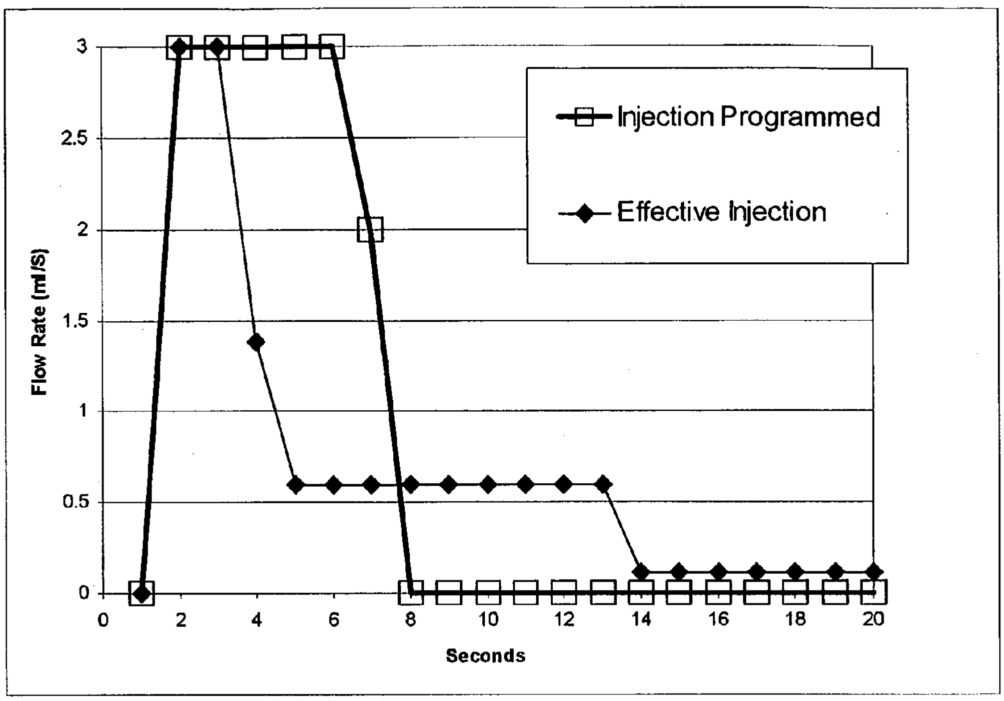
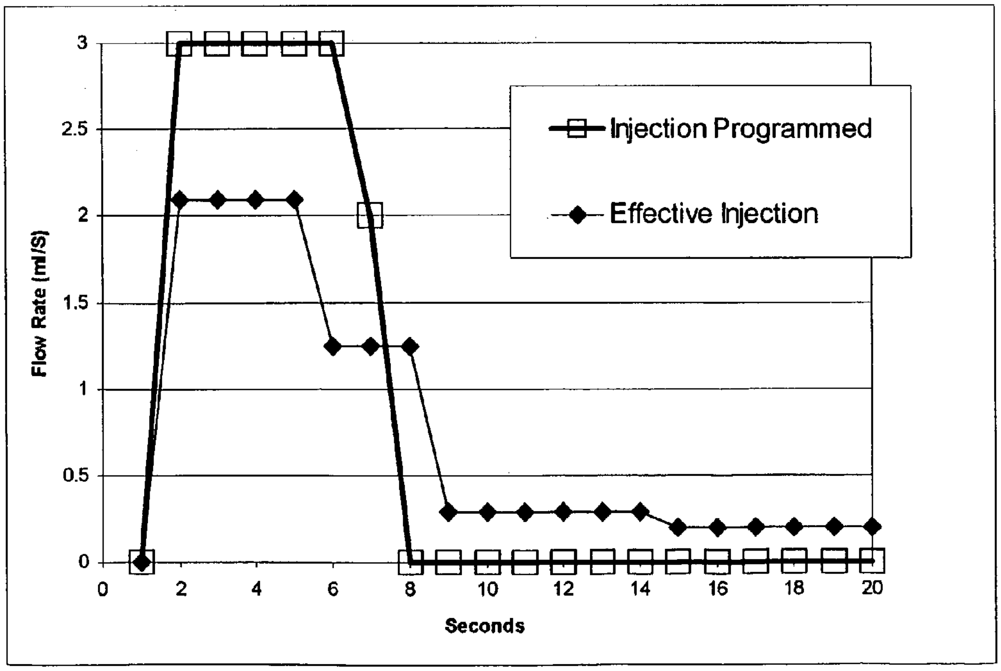
Fig. 18B

SYSTEMS AND METHODS OF DETERMINING PATIENT TRANSFER FUNCTIONS AND MODELING PATIENT RESPONSE TO A PHARMACEUTICAL INJECTION

CROSS-REFERENCE TO RELATED APPLICATION

The application claims benefit of U.S. Provisional Patent Application Ser. No. 60/628,201, filed Nov. 16, 2004, the disclosure of which is incorporated herein by reference.

BACKGROUND OF THE INVENTION

The present invention relates generally to modeling of the propagation of a pharmaceutical in a patient, and, particularly, to modeling of contrast media propagation in a patient for use in imaging procedures.

References set forth herein may facilitate understanding of the present invention or the background of the present invention. Inclusion of a reference herein, however, is not intended to and does not constitute an admission that the reference is available as prior art with respect to the present invention.

Various contrast media are injected into a patient for many diagnostic and therapeutic imaging procedures such as X-ray procedures (including, for example, angiography, venography and urography), computed tomography (CT), magnetic resonance imaging (MRI), ultrasonic imaging, light based imaging, and positron emission tomography (PET). The CT scanner has, for example, become an indispensable modern, diagnostic imaging tool. It enables the precise measurement of anatomical structures, and in some instances, physiologic processes in 2, 3 and 4 dimensions. The imaging of soft tissue, vasculature, and other structures is not easily accomplished with CT scanners because these structures do not differentially attenuate X-Rays to an appreciable degree. To overcome these limitations, a radio-absorbing or radio-opaque drug or contrast is injected, commonly into the peripheral venous circulation. The contrast agent used for CT imaging is typically a water-soluble salt that binds three or more Iodine atoms within a benzene structure. Iodine attenuates X-Rays in the energy ranges used in medical imaging procedures. A computer-controlled pump or injector injects a precise volume of contrast agent at flow rates typically ranging from 0.5 to 6 ml/s (pressures generated up to 300 psi) into a patient's venous system before a scan is made. Examples of front loading syringe injectors commonly used in CT procedures are disclosed, for example, in U.S. Pat. Nos. 5,300,031, 5,383,858 and 6,652,489, the disclosure of which is incorporated herein by reference.

The MultiDetector CT scanners (MDCT) now enable clinicians to perform unparalleled diagnostic scans of patient anatomy and physiology. With such new technologies, however, arise new challenges for application in daily practice. Despite the breakthroughs in volumetric coverage and image resolution, the new generation of CT scanners still requires the administration of iodinated contrast agent to achieve the best image and diagnosis. Moreover, the importance of timing of the scan to coincide with optimal contrast concentration can be increased in the case of MDCT.

The delivery of contrast agent is generally open-loop in the sense that the injection system does not incorporate knowledge or estimates of the drug's interaction with the physiology into its control scheme. The injection system delivers exactly the amount of contrast agent programmed at the specified rate. This methodology works well when a scan takes a substantial amount of time so that the early pharmacokinetics of the drug does not influence the quality of the diagnostic scan. This methodology also works well when the object of the scan is an assessment of perfusion, that is drug uptake, into, for example, parenchyma or suspected carcinomas. Advances in scanning technology enable the acquisition of images in very short time periods (seconds). This trend, coupled with the increasing desire to produce volumetric renderings of anatomical structures (like the heart, its coronary vasculature, and the great vessels leading to and from it), requires that the early pharmacokinetics and pharmacodynamics of the contrast be considered. Ideally, the attenuation curve produced by the presence of contrast agent in a large blood vessel is preferably uniform (flat) and sufficiently similar across regions of the patient to facilitate volumetric rendering and accurate diagnosis, and the imaging scan is timed to coincide with optimal contrast concentration in the region(s) of interest.

Differences in dosing requirements for different patients during imaging and other procedures have been recognized. For example, U.S. Pat. No. 5,840,026, assigned to the assignee of the present invention, the disclosure of which is incorporated herein by reference, discloses devices and methods to customize the injection to the patient using patient specific data derived before or during an injection. Although differences in dosing requirements for medical imaging procedures based upon patient differences have been recognized, conventional medical imaging procedures continue to use pre-set doses or standard delivery protocols for injecting contrast media during medical imaging procedures. Given the increased scan speed of recently available CT scanners including MDCT scanners, single phase injections are dominant over biphasic injections in regions of the world where such fast scanners are used. Although using fixed protocols (whether uniphasic, biphasic or multiphasic) for delivery simplifies the procedure, providing the same amount of contrast media to different patients under the same protocol can produce very different results in image contrast and quality. Furthermore, with the introduction of the newest MDCT scanners, an open question in clinical practice and in the CT literature is whether the standard contrast protocols used with single-slice, helical scanners will translate well to procedures using the MDCT machines. Cademartiri, F. and Luccichenti, G., et al. (2004). "Sixteen-row multislice computed tomography: basic concepts, protocols, and enhanced clinical applications." Semin Ultrasound CT MR 25(1): 2-16.

A few studies have attempted quantitative analyses of the injection process during CT angiography (CTA) to improve and predict arterial enhancement. For example, Bae and coworkers developed pharmacokinetic (PK) and dynamic models of the contrast behavior and solved the coupled differential equation system with the aim of finding a driving function that causes the most uniform arterial enhancement. K. T. Bae, J. P. Heiken, and J. A. Brink, "Aortic and hepatic contrast medium enhancement at CT. Part I. Prediction with a computer model," *Radiology*, vol. 207, pp. 647-55, 1998; K. T. Bae, "Peak contrast enhancement in CT and MR angiography: when does it occur and why? Pharmacokinetic study in a porcine model," *Radiology*, vol. 227, pp. 809-16, 2003, K. T. Bae et al., "Multiphasic Injection Method for Uniform Prolonged Vascular Enhancement at CT Angiography: Pharmacokinetic Analysis and Experimental Porcine Method," *Radiology*, vol. 216, pp. 872-880, 2000, U.S. Pat. Nos. 5,583,902, 5,687,208, 6,055,985, 6,470,889 and 6,635,030, the disclosures of which are incorporated herein by reference. An inverse solution to a set of differential equations of a simplified compartmental model set forth by Bae et al. indicates that an exponentially decreasing flow rate of contrast medium may result in optimal/constant enhancement in a CT imaging procedure.

Bae's PK approach for deriving uniform image enhancement relies upon many physiological parameters that may not be readily available to a clinician, such as central blood volume, diffusion rates, and cardiac output. Not having explicit measurements of cardiac output is a substantial drawback to Bae's approach, despite attempts to approximate the value based upon the patient's age, weight, and height. Furthermore, there is no consideration for implementation of the PK models in a controller framework. The injection profiles computed by inverse solution of the PK model are profiles not readily realizable by CT power injectors, without major modification. Moreover, the PK model of Bae does not consider the effects of pulsatile flow, vessel compliance, and local blood/contrast parameters (i.e., viscosity).

Fleischmann and coworkers treat the cardiovascular physiology and contrast kinetics as a "black box" and determine its impulse response by forcing the system with a short bolus of contrast (approximating an unit impulse). In that method, one performs a Fourier transform on the impulse response and manipulates this transfer function estimate to find the optimal injection trajectory. D. Fleischmann and K. Hittmair, "Mathematical analysis of arterial enhancement and optimization of bolus geometry for CT angiography using the discrete Fourier transform," *J Comput Assist Tomogr*, vol. 23, pp. 474-84, 1999, the disclosure of which is incorporated herein by reference.

The administration of contrast agent is commonly uniphasic—100 to 150 mL of contrast at one flow rate, which results in a non-uniform enhancement curve. See, for example, D. Fleischmann and K. Hittmair, supra; and K. T. Bae, "Peak contrast enhancement in CT and MR angiography: when does it occur and why? Pharmacokinetic study in a porcine model," *Radiology*, vol. 227, pp. 809-16, 2003, the disclosures of which are incorporated herein by reference. Fleischmann and Hittmair present a scheme that attempts to tailor the administration of contrast agent into a biphasic injection tailored to the individual patient with the intent of optimizing imaging of the aorta. A fundamental difficulty with controlling the presentation of CT contrast agent is that hyperosmolar drug diffuses quickly from the central blood compartment. Additionally, the contrast is mixed with and diluted by blood that does not contain contrast. The mixing and dilution of the contrast medium is reflected by a peaked and distorted enhancement curve as exemplified in FIG. 1.

Fleischmann proscribes that a small bolus injection, a test injection, of contrast agent (16 ml of contrast at 4 ml/s) be injected prior to the diagnostic scan. A dynamic enhancement scan is made across a vessel of interest. The resulting processed scan data (test scan) is interpreted as the impulse response of the patient/contrast medium system. Fleischmann derives the Fourier transform of the patient transfer function by dividing the Fourier transform of the test scan by the Fourier transform of the test injection. Assuming the system is a linear time invariant (LTI) system and that the desired output time domain signal is known (a flat diagnostic scan at a predefined enhancement level) Fleischmann derives an input time signal by dividing the frequency domain representations of the desired output by that of the patient transfer function.

The approach of Fleischmann may be promising in the fact that it derives a representation of the patient based upon a known test injection. Because the method of Fleischmann et al. computes input signals that are not realizable in reality as a result of injection system limitations (for example, flow rate limitations), one must truncate and approximate the computed continuous time signal. Because of the inaccuracies introduced by that step, the computed idealized input trajectories are not optimal. Furthermore, it is unclear if the linearity assumption holds for all patients and pathophysiologies. Finally, it is unclear if the enhancement curves generated by his method are any more uniform than those generated by simple biphasic injections.

Various models have also been developed for pharmaceuticals other than contrast medial. For example, Fisher and Teo, "Optimal insulin infusion resulting from a mathematical model of blood glucose dynamics", *IEEE Trans Biomed Eng*, vol. 36(4), pp. 479-486, 1989, the disclosure of which is incorporated herein by reference, modeled the dynamics of glucose and insulin with the aim of generating optimal insulin infusion parameters. They treat the problem as a classic optimization problem by applying a quadratic performance criterion and solving the algebraic Ricatti equations. They discovered that impulse control was the superior approach compared to constant infusion, sub-optimal control and no regulation of the insulin injection.

Jacobs, "Algorithm for optimal linear model-based control with application to pharmacokinetic model-driven drug delivery", *IEEE Trans Biomed Eng*, vol. 37(1), pp. 107-109, 1990, the disclosure of which is incorporated herein by reference, presented a control algorithm for the regulation of anesthetic drugs that places a pharmacokinetic model in parallel with the actual drug process. A clinician determines the target plasma concentration.

Wada and Ward, "The hybrid model: a new pharmacokinetic model for computer-controlled infusion pumps", IEEE Trans. Biomed Eng, vol. 41(2), pp. 134-142, 1994, the disclosure of which is incorporated herein by reference, derived a 3 compartment pharmacokinetic model similar to the approach taken by Bee and used this in a hybrid control scheme in an attempt to regulate the plasma concentration of anesthetic (the upload alienating). They were attempting to model the recirculation effect of the agent through the blood stream, as well, which they modeled by inserting transport delays in their simulations. They were able to generate simulation with prediction errors under 5%.

Wada and Ward "Open loop control of multiple drug effects in anesthesia", IEEE Trans. Biomed Eng, vol. 42(7), pp. 666-677, 1995, the disclosure of which is incorporated herein by reference, also applied their hybrid pharmacokinetic (PK) model to control multiple effects of anesthetic drugs. Their control scheme requires an anesthesiologist to set the allowable side-effect levels (expressed as a plasma concentration).

Neatpisarnvanit and Boston, "Estimation of plasma insulin from plasma glucose", *IEEE Trans Biomed Eng*, vol. 49(11), pp. 1253-1259, 2002, the disclosure of which is incorporated herein by reference, applied a recursive least square parameter estimation approach to predict the plasma concentration of glucose and insulin. Their approach resulted in predictions that matched plasma levels of glucose and insulin in 6 of 7 patients (experimental data gathered via the IntraVenous Glucose Tolerance Test) and agreed favorably.

Gentilini et al. "A new paradigm for the closed-loop intraoperative administration of analgesics in humans", *IEEE Tran Biomed Eng*, vol. 49(4), pp. 289-299, 2002, the disclosure of which is incorporated herein by reference, proposed a model predictive control (MPC) approach for controlling the plasma concentration of the opiate alfentanil with a computer controlled infusion pump. The pharmacokinetic model was a 3-compartment model describing the distribution of the opiate in a human. The controller relied upon an observer that estimates plasma concentrations of the drug based on measurements of mean arterial pressure and a PK model running in parallel. Gentilini et al. placed constraints on the maximum concentration to prevent overdosing. They also filtered disturbances in the mean arterial pressure measurements and allowed for the controller to act faster or slower depending on the state of the patient (that is, hypo vs. hypertensive).

SUMMARY OF THE INVENTION

The present invention provides generally improved devices, systems and methods that facilitate the determination/creation of or the adjustment of a patient transfer function, or model (or the parameters of a model) of patient response to a pharmaceutical injection. The patient transfer function or model can be based, for example, upon information known or measured before the start of the procedure, from a test injection, and/or from feedback during the procedure itself to improve or optimize pharmaceutical delivery (for example, contrast concentration in one or more regions of interest).

In one aspect, the present invention provides a method of delivering a contrast enhancing fluid to a patient using an injector system, including: determining at least one patient transfer function for the patient based upon data specific to the patient, the at least one patient transfer function providing a time enhancement output for a given input; determining a desired time enhancement output; using the at least one patient transfer function to determine an injection procedure input; and controlling the injector system at least in part on the basis of the determined injection procedure input. The injection procedure input can determined considering at least one operational limitation or constraint of the injector system.

The at least one patient transfer function can, for example, be determined using a system identification model comprising parameters related to physiological parameters of the patient. The system identification model is preferably discretizable.

The method can further include the steps of: developing an initial patient transfer function using estimates of at least one physiological parameter of the patient; performing an injection; and revising the patient transfer function based upon at least one time enhancement output of the injection. At least one patient physiological parameter can be measured from the at least one time enhancement output. The injection can be a test injection performed prior to a diagnostic imaging procedure or an injection performed during the imaging procedure.

Time enhancement outputs resulting from the test injection can be measured for at least two different regions of interest. At least one difference between the time enhancement outputs can, for example, provide a measure of at least one patient physiological parameter. The at least one patient physiological parameter can be a parameter of the cardiopulmonary system The at least one patient physiological parameter can, for example, be cardiac output, blood volume in a region, a rate transfer term or a transit delay. In one embodiment, a first time enhancement output is measured in the ascending aorta or the descending aorta and a second time enhancement output is measured in the pulmonary artery trunk.

The at least one patient transfer function can also be determined by the steps: collecting data corresponding to a time response curve resulting from injection of the fluid; and determining at least one mathematical model describing the data.

In one embodiment, the mathematical model is not determined by a continuous or a discrete-time Fourier deconvolution of the data. The model can be a parametric model. The model can, for example, be a moving average or an autoregressive moving average. The mathematical model can assume linearity and time invariance.

The model can also be a non-parametric model determined by a spectral estimation technique. The spectral estimation technique can, for example, be Welch's method, Bartlett's method, a multiple signal classification (MUSIC) method, or the Periodogram method. Data can be collected during at least one test injection prior to an imaging injection.

The at least one patient transfer function of the present invention can be updated with data collected during the imaging injection.

As described above, the at least one patient transfer function can be determined at least in part on the basis of at least one injection. The at least one injection can be a test injection performed prior to a diagnostic imaging procedure. In one embodiment, the test injection comprises injection of contrast medium followed by injection of a non-contrast fluid. The non-contrast fluid can be injected at substantially the same volumetric flow rate as a flow rate of contrast medium preceding the injection of non-contrast fluid. The non-contrast fluid can be saline.

More than one test injection can be performed. For example, one test injection can include injection of contrast medium only and another test injection can include injection of contrast medium followed by injection of a non-contrast fluid.

The injection procedure input of the present invention can be determined using an analytical solution or using a numerical, constrained optimization technique. In one embodiment, the numerical, constrained optimization technique is a weighted least-squared numerical optimization.

The injection procedure input can, for example, be optimized with respect to one or more considerations. For example, the injection procedure input can be optimized to minimize the mass of a contrast enhancing agent in the contrast enhancing fluid delivered to the patient.

Examples of contrast enhancing agents suitable for use in connection with the present invention include, but are not limited to, iodine, xenon and gadolinium. The contrast enhancing fluid can, for example, be a CT contrast enhancing fluid, a MRI contrast enhancing fluid, an ultrasound enhancing imaging fluid or a radioactive contrast enhancing fluid.

In one embodiment of the present invention, at least two patient transfer functions are determined and the injection procedure input is determined on the basis of one of the patient transfer function. For example, a first patient transfer function can be determined using a system identification model comprising parameters related to physiological parameters of the patient, and a second patient transfer function can be determined using a mathematic model determined by collecting data corresponding to a time enhancement curve resulting from injection, the mathematical model describing the data. A determination can, for example, be made as to which patient transfer function provides the best correlation between a given input and a resulting output.

In another aspect, the present invention provides a method of determining at least one patient physiological parameter from an imaging procedure including: measuring time enhancement outputs for at least two different regions of interest and determining at least one difference between the time enhancement outputs to provide a measure of the at least one patient physiological parameter. The at least one patient physiological parameter can, for example, be a parameter of the cardiopulmonary system. The at least one patient physiological parameter can, for example, be cardiac output, blood volume in a region, a rate transfer term or a transit delay. In one embodiment, a first time enhancement output is measured in the ascending aorta or the descending aorta and a second time enhancement output is measured in the pulmonary artery trunk.

In a further aspect, the present invention provides an injector system for the delivery of a fluid to a patient including: an injector and a controller in communicative connection with the injector. The controller includes (for example, has stored in a memory in operative connection therewith) at least one patient transfer function determined for the patient based upon data specific to the patient. The at least one patient transfer function provides a time enhancement output for a given input. The controller includes a processor (for example, a digital microprocessor) to determine an injection procedure input for a desired time enhancement output using the at least one patient transfer function.

The injection procedure input can be determined considering at least one physical limitation or constraint of the injector. The injection procedure input can, for example, be determined using an analytical solution or a numerical, constrained optimization technique. The numerical, constrained optimization technique can, for example, be a weighted least-squared numerical optimization. The injection procedure input can optimized to, for example, minimize the mass of a contrast enhancing agent in the contrast enhancing fluid delivered to the patient.

The contrast enhancing agent can, for example, be iodine, xenon or gadolinium. The contrast enhancing fluid can, for example, be a CT contrast enhancing fluid, a MRI contrast enhancing fluid, an ultrasound enhancing imaging fluid or a radioactive contrast enhancing fluid.

In another aspect, the present invention provides an imaging system including an imager to create an image of a region of interest of a patient; an injector adapted to inject a contrast medium; and a controller in operative communication with the injector to control the injector. The controller includes at least one patient transfer function determined for the patient based upon data specific to the patient. The at least one patient transfer function provides a time enhancement output for a given input. The controller also includes a processor to determine an injection procedure input for a desired time enhancement output using the at least one patient transfer function as described above.

In several embodiments of the present invention, spectral analysis and parameter estimation of patient response/scan data obtained during short injections of contrast agent are used in the development of a control paradigm capable of providing closed loop control of contrast agent administration.

In one aspect, the present invention provides a method of modeling propagation of a pharmaceutical fluid in a patient, including: collecting data corresponding to a time response curve resulting from injection of the fluid; and determining at least one mathematical model describing the data. The mathematical model can, for example, be a model which is not determined by a continuous or a discrete-time Fourier deconvolution of the data.

The model can be a parametric model such as a moving average model or an autoregressive moving average model. The model can also be a parametric model including parameters fit for the measured data. One can, for example, assume linearity and time invariance in the mathematical model. The model can also be a non-parametric model determined by a spectral estimation technique. Suitable spectral estimation techniques include, but are not limited to, Welch's method, Bartlett's method, a multiple signal classification (MUSIC) method, or the Periodogram method.

The injected fluid can, for example, be a contrast medium used in an imaging procedure and the data collected can correspond to a time enhancement curve resulting from injection of the contrast medium.

The collected data for a time response curve or time enhancement curve can be collected during at least one test injection prior to an imaging injection. The model can also be determined and/or updated with data collected during the imaging (or other procedural) injection. In one embodiment, a test injection includes injection of contrast medium followed by injection of a non-contrast fluid. The non-contrast fluid can, for example, be injected at substantially the same volumetric flow rate as a flow rate of contrast medium preceding the injection of non-contrast fluid. The non-contrast fluid can, for example, be saline. More than one test injection can be performed. In one such embodiment, one test injection includes injection of contrast medium only and another test injection includes injection of contrast medium followed by injection of a non-contrast fluid.

In another aspect, the present invention provides a method of controlling injection of a pharmaceutical fluid into a patient using an injector in a medical procedure, including: collecting data corresponding to a patient response curve resulting from injection of the fluid; determining at least one mathematical model describing the data; and controlling the injector during the medical procedure to control injection of the fluid into the patient to create patient response at least in part on the basis of the mathematical model. The mathematical model can, for example, be a model which is not determined by a continuous or a discrete-time Fourier deconvolution of the data.

The medical procedure can, for example, be a medical imaging procedure using an imaging scanner and the collected data can correspond to a time enhancement curve resulting from injection of the contrast medium. The injector can be controlled to control injection of the contrast medium into the patient to create an image of a region of interest at least in part on the basis of the mathematical model.

The injector can also be controlled at least in part on the basis of information regarding the patient response during the imaging procedure. Further, the injector can be controlled at least in part on the basis of information on at least one measured physiological variable of the patient. The measured physiological variable can be used to alter the output of the mathematical model.

In one embodiment, the step of controlling the injector includes commencing injection of the contrast medium at one time and commencing an image scan of the region of interest at a second time determined at least in part on the basis of the mathematical model. The second time can be determined on the basis of a prediction of a time of attainment of a predetermined enhancement level as determined by the mathematical model.

In another aspect, the present invention provides an injection system including: an injector; and a injector controller in operative communication with the injector to control the injector. The injector controller controls injection of a fluid based upon at least one mathematical model as described above. In that regard, the mathematical model can be determined by collecting data corresponding to a time enhancement curve resulting from injection of the contrast medium. The mathematical model can, for example, be a model that is not determined by a continuous or a discrete-time Fourier deconvolution of the data. The controller can, for example, include a computer having at least one processing unit and at least one memory. The memory has stored therein a computer program to determine the mathematical model.

In a further aspect, the present invention provides a method of controlling injection of a contrast medium into a patient using an injector in a medical imaging procedure using an imaging scanner, including: determining at least one mathematical model to predict a time enhancement response resulting from injection of the contrast medium; determining an injection protocol to approximate a predetermined time enhancement response in the patient by determining a constrained input solution to the mathematical model; and using the injection protocol to control the injector during the medical imaging procedure to control injection of the contrast medium into the patient to create an image of a region of interest.

The method can further include the step of changing the injection protocol as a result of feedback regarding the time enhancement response during the imaging procedure. The method can further include the step of changing the injection protocol as a result of data regarding at least one patient physiological parameter during the imaging procedure.

In one embodiment, the step of determining an injection protocol to approximate the predetermined time enhancement response is accomplished using a numerical solver or a numerical optimizer. The constrained input solution to the mathematical model can, for example, be constrained by at least one operational limitation of the injector. The constrained input solution to the mathematical model can also or alternatively be constrained by at least one operational limitation related to patient safety or comfort.

The injection of the contrast medium can, for example, be commenced at one time and an image scan of the region of interest can be commenced at a second time determined at least in part on the basis of the mathematical model. The second time can, for example, be determined on the basis of a prediction of a time of attainment of a predetermined enhancement level as determined by the mathematical model.

The at least one mathematical model can be a patient transfer function for the patient based upon data specific to the patient. The patient transfer function provides a time enhancement output for a given input. The first patient transfer function can, for example, be determined using a system identification model comprising parameters related to physiological parameters of the patient or using a mathematic identification model determined by collecting data corresponding to a time enhancement curve resulting from injection of the patient, wherein the mathematical identification model describes the data.

In another aspect, the present invention provides a system for effecting a medical procedure including: a sensing system to detect a patient response; an injector adapted to inject a pharmaceutical fluid; and a controller in operative communication with the injector to control the injector. The injector controller controls injection of a fluid based upon at least one mathematical model. The mathematical model is determined by collecting data from the sensing system corresponding to a time response curve resulting from injection of the fluid. The mathematical model can, for example, be a model which is not determined by a continuous or a discrete-time Fourier deconvolution of the data.

In another aspect, the present invention provides an imaging system including: an imager to create an image of a region of interest of a patient; an injector adapted to inject a contrast medium; and a controller in operative communication with the injector to control the injector. The injector controller controls injection of the contrast medium based upon at least one mathematical model. The mathematical model is determined by collecting data from the imager corresponding to a time enhancement curve resulting from injection of the contrast medium. The mathematical model can, for example, be a model which is not determined by a continuous or a discrete-time Fourier deconvolution of the data.

In another aspect, the present invention provides a method of controlling injection of a pharmaceutical fluid into a patient using an injector having a controller in communicative connection with a computer memory in a medical procedure, including: collecting data corresponding to a patient response curve resulting from injection of the fluid; choosing at least one mathematical model from a plurality of mathematical models stored in the computer memory to describe the data; adapting the model to the collected data; and controlling the injector via the controller during the medical procedure to control injection of the fluid into the patient to create patient response at least in part on the basis of the mathematical model.

In a further aspect, the present invention provides a system for creating an image of a region of interest of a patient including: an imaging device for measuring a property of the patient over a region of interest; an injector for injecting a pharmaceutical into the patient; at least one standard (or reference) region that is also measured by the imaging device; and a computation algorithm that adjusts or corrects measurements of the property over the patient's region of interest based upon the measurements in the standard region. A suitable standard region can be outside of the patient. A suitable standard region can also be a region of the patient.

In still a further aspect, the present invention provides a method of creating an image of a region of interest in a patient including: measuring a property of the patient over the region of interest using an imaging device; injecting a pharmaceutical into a patient, measuring at least one region of a standard with the imaging device; and correcting or adjusting measurements of the property over the patient's region of interest based upon the measurements in the standard region.

Benefits provided by various embodiments of this invention include, but are not limited to: more consistent enhancement for subsequent image processing, reduced contrast or fluid loading for some patients, increased contrast dose to achieve sufficient image contrast when needed, reduced chance of extravasation, reduced image artifacts, reduced number of retakes, all slices containing optimal image contrast, increased consistency among scans observing a progression of disease or treatment over time, and optionally faster imaging times.

BRIEF DESCRIPTION OF THE DRAWINGS

Other aspects of the invention and their advantages will be discerned from the following detailed description when read in connection with the accompanying drawings, in which:

FIG. 2*a* represents an example of a patient's response to a test injection.

FIG. 2*c* illustrates a patient impulse response, h(n), from empirical, dynamic CT data from a region of interest in the descending aorta of a human (Fleischmann and Hittmair 1999).

FIG. 18A illustrates an effective injection profile of a test injection without saline flush for one patient.

FIG. 18B illustrates an effective injection profile of a test injection without saline flush for a different patient.

DETAILED DESCRIPTION OF THE INVENTION

Figure 1A:
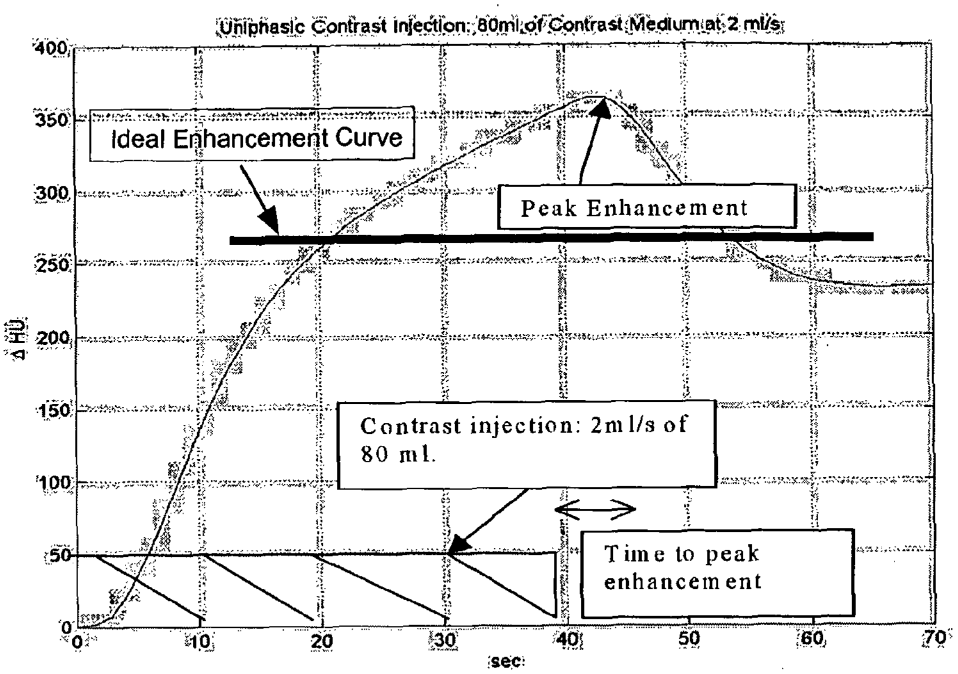
FIG. 1*a* illustrates a typical time-enhancement curve obtained with a single phase injection profile for a contrast-enhanced CT scan of a blood vessel.

FIG. 1A illustrates a typical time-enhancement curve obtained with a single phase contrast-enhanced CT scan of a blood vessel. The units HU are Houndsfield Units, a measure of X-ray absorption density that is translated into signal intensity in an image. FIG. 1A illustrates a peak enhancement at a time of about 45 seconds. In many imaging procedures, the time-enhancement curve is preferably uniform around a specified level (as illustrated by the thick black line in FIG. 1A). When the curve is not uniform or flat, a less than optimum image may result in an erroneous diagnosis in such imaging procedure. As advances in scanning technology enable image acquisition in less time, uniformity of enhancement over longer time periods may decrease somewhat in importance, but proper timing of a scan relative to contrast injection and avoidance of too much contrast or too little contrast remain important.

Figure 1B:
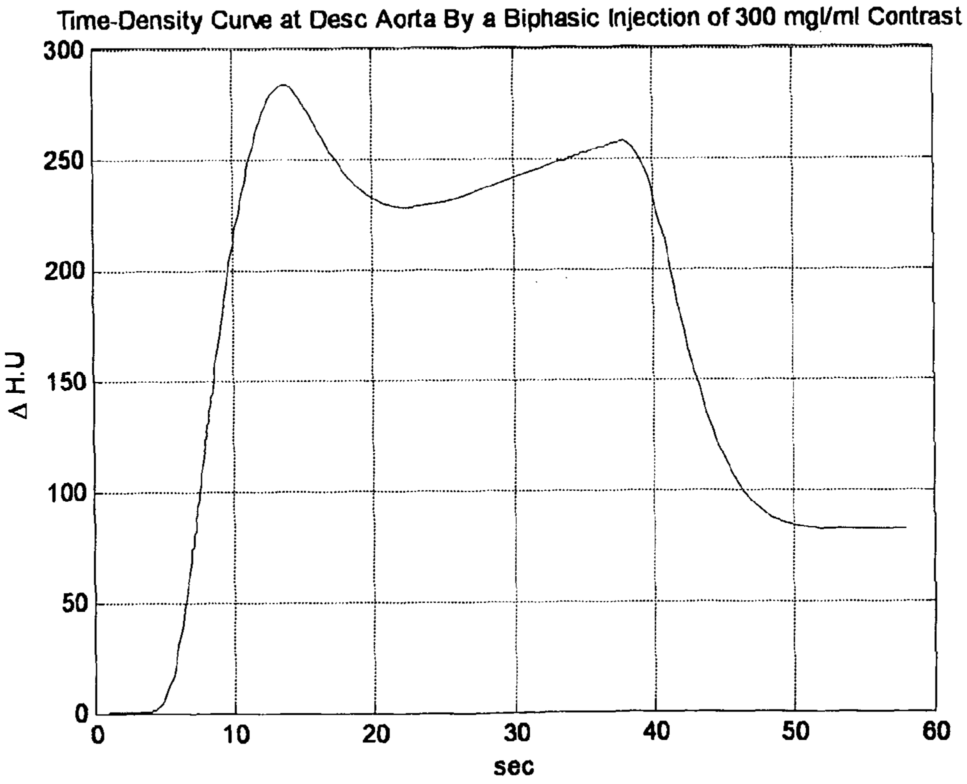
FIG. 1*b* illustrates a typical time-enhancement curve obtained with a dual phase or bi-phasic injection profile for a contrast-enhanced CT scan of a blood vessel.

FIG. 1B illustrates a typical time-enhancement curve obtained with a dual phase or bi-phasic contrast-enhanced CT scan of a blood vessel. The enhancement curvature is somewhat flatter or more uniform. However, the amount of flatness can vary from patient to patient and thus still produce a less than optimum image.

Figure 2B:
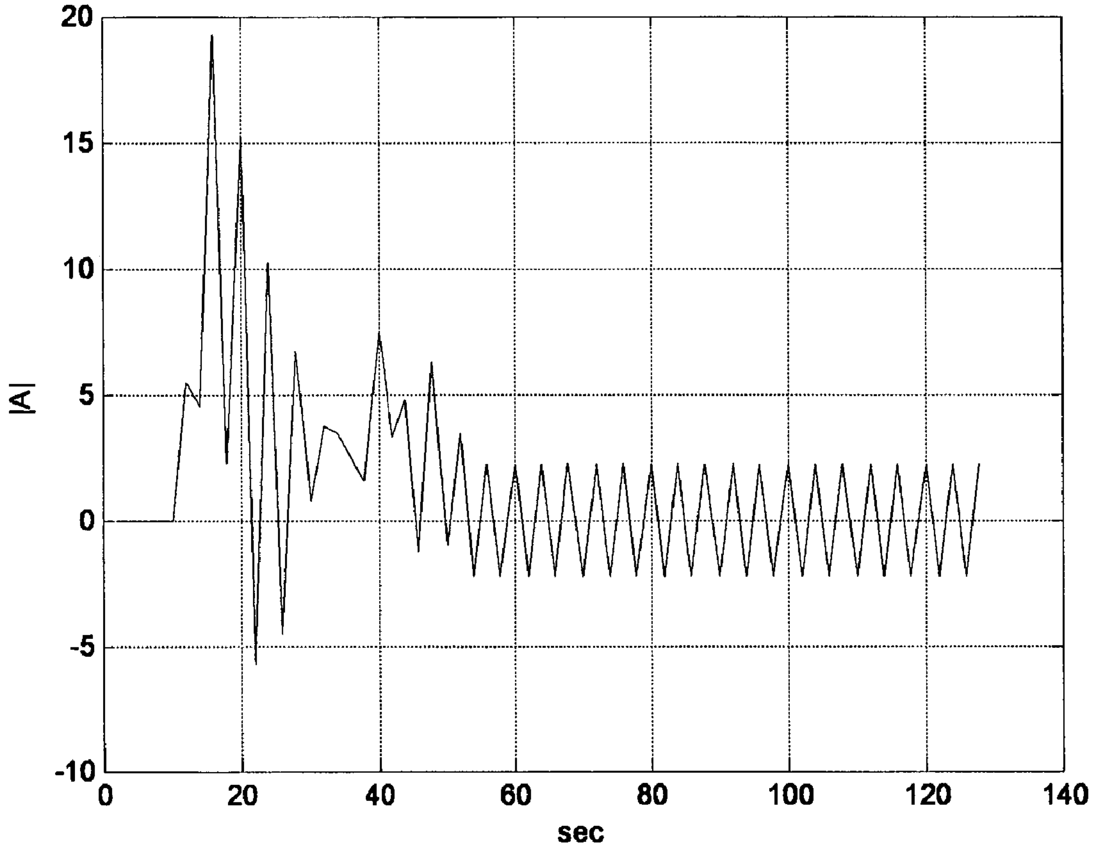
FIG. 2*b* illustrates an estimated impulse response of the patient/contrast agent system in the time domain derived by a discrete-time Fourier deconvolution of the scanner output divided by the contrast input function using data from Fleischmann and Hittmair, supra.

FIG. 2A illustrates a typical patient response to a test injection. FIGS. 2B and 2C illustrate a typical patient impulse response. FIG. 2B is the response in the time domain and FIG. 2C is h(n) in the frequency domain, as published in D. Fleischmann and K. Hittmair, supra. The patient impulse responses are derived from the patient's response to a test injection, for example through Fourier deconvolution in the frequency domain or in the time domain. In the injection plot of FIG. 2C, data were captured every 2 seconds with a CT scanner.

In one embodiment of the present invention, a model predictive control (MPC) controller architecture for contrast enhancement is set forth. In the embodiment illustrated in FIG. 3, the control process uses an enhancement curve generated from a test injection to, for example, estimate the parameters of a multi-pole/zero model of the patient system if assuming an LTI system, or deriving an appropriate kernel function if one relaxes the time-invariant assumptions. One can also readily relax the linearity assumption. An analogous example of a time-varying system is an electrical circuit with resistors and capacitors whose values vary with respect to time and potentially other independent variables. Typically, circuit analysis considers the resistance and capacitors to be fixed at a single value regardless of time.

Figure 3:
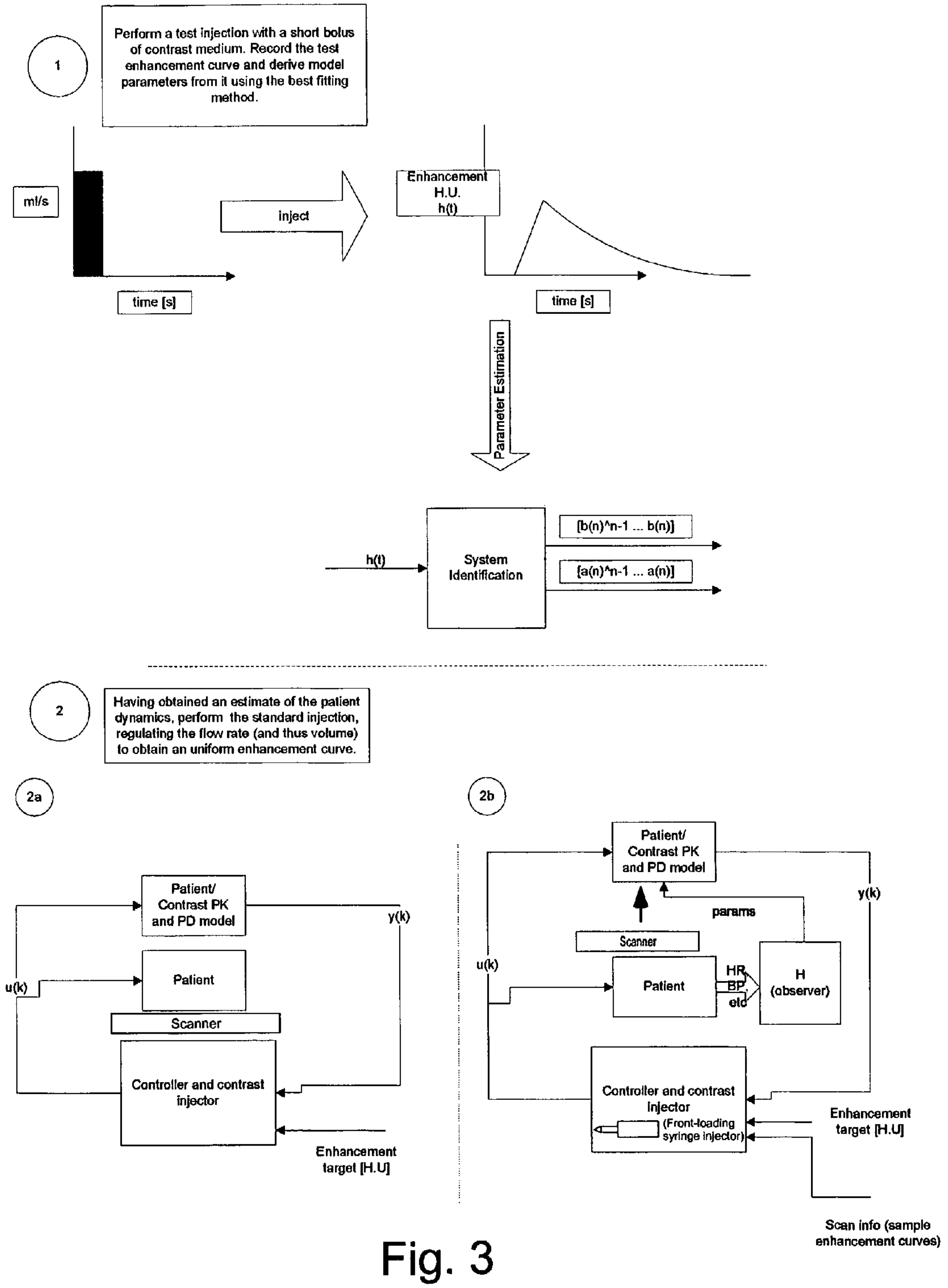
FIG. 3 illustrates one embodiment of an MPC controller architecture of the present invention for improving enhancement of CT images with contrast medium injectors.

The parameters identified in the test injection step can then be used by a PK/PD (pharmo-dynamic) model used to update the controller during the full injection step with the target end-points being, for example, a predefined, uniform enhancement value. As illustrated in FIG. 3, the controller can also accommodate feedback signals from the scanner (i.e. enhancement values (EV)) or estimated parameters from an observer (i.e., heart rate (HR), blood pressure (BP), respiration rate & depth, patient weight) that can assist in reducing controller error. Feedback from a scanner to control an injector is described, for example, in U.S. Pat. No. 6,397,098, assigned to the assignee of the present invention, the disclosure of which is incorporated herein by reference. A Model Predictive Control algorithm can, for example, be implemented that adjusts the input trajectory of the contrast administration based upon instantaneous enhancement data from the scanner gathered at one time step. If the actual enhancement value differs from that predicted by the model generated in the identification step (for example, in the least squares sense) then the control algorithm can adjust the input flow rate in an attempt to bring the instantaneous enhancement value at a subsequent time step closer to that predicted by the model. One can derive a higher fidelity model of the contrast propagation with knowledge of the patient's heart rate acquired from a heart rate monitor (ECG), pulse oximeter, or blood pressure monitor.

In one embodiment of FIG. 3, the model of the present invention generates an estimate of a patient transfer function, H(z), via pole-zero modeling (ARMA techniques) and performs a constrained numerical optimization to determine an input signal (that is, an injection protocol) that will generate the desired output response (for example, a flat enhancement scan—see FIG. 1). Alternatively, one can use a pole-placement algorithm, given an estimate of H(z), to better control the output response.

The structure of the patient transfer function can be determined by analyzing patient impulse responses, h(n), gathered during clinical investigations. There are apparently no published analyses of the underlying spectral content of the patient transfer functions. An ARMA modeling technique can, for example, be used to generate the coefficients for a rational transfer function of the form:

$$H(z) = \frac{B_q(z)}{A_p(z)} = \frac{\sum_{k=0}^{q} b_q(k) z^{-k}}{1 + \sum_{k=1}^{p} a_p(k) z^{-k}} \qquad \text{Equation (1)}$$

In several embodiments, the present invention provides a paradigm for administering iodinated contrast medium that allows for the tailoring of contrast protocols to an individual patient and to a region of interest to be scanned. Avenues for determining the patient transfer function between the administration site of the contrast and the enhancement territory of interest include model dependent approaches and model independent approaches. Both approaches or schemes are a form of system identification, wherein the system includes the drug and patient (cofactors including, for example, the scan settings, the territory or region of interest, and the pathophysiology). The outcome of both approaches results in an estimate of the contrast media's dynamics. Knowledge of the system's dynamics can, for example, be used in an optimization step to determining injection protocols for maximizing the signal to noise ratio (SNR), while minimizing iodine load/dose to the patient (given the constraints of the injection system, which include, for example, positive flow rates, maximum flow rate given the viscosity of the contrast and gauge of the attached catheter, and volume of contrast media).

A. A Priori Model-Dependent Identification

Figure 4:
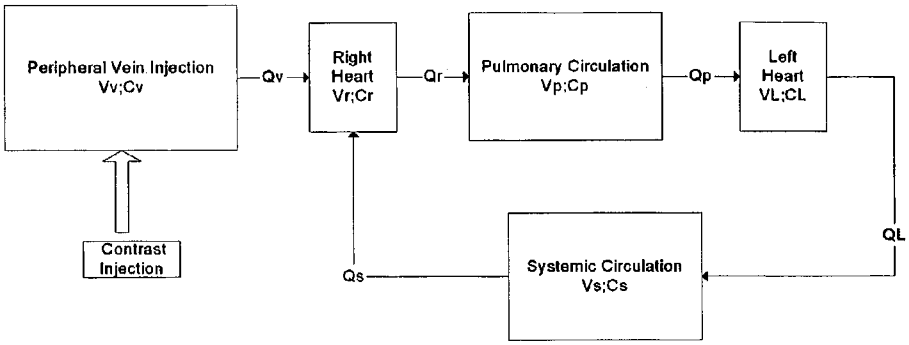
FIG. 4 sets forth a reduced PK model of X-Ray contrast, as published by Bae, Heiken et al. 1998.

Bae et al. devised a reduced order, or hybrid, PK model of contrast media propagation. Bae, K. T., J. P. Heiken, et al. (1998). "Aortic and hepatic contrast medium enhancement at CT. Part I. Prediction with a computer model." Radiology 207(3): 647-55 and Bae, K. T., H. Q. Tran, et al. (2000). "Multiphasic injection method for uniform prolonged vascular enhancement at CT angiography: pharmacokinetic analysis and experimental porcine model." Radiology 216(3): 872-80, the disclosures of which are incorporated herein by reference. The modeling approach in that work recognized that the full body physiologic pharmacokinetic model taught in Bae, Heiken et al, 1998 supra, was too large and included too may unknowns to feasibly compute on a per patient basis. Bae and colleagues, therefore, approximated large parts of the anatomy with single compartments and, because first-pass enhancement dynamics are of interest, removed the capillary transfer compartments. The resulting, reduced-order model is illustrated in FIG. 4. In FIG. 4, V are the fluid volumes of the respective "compartments", C are the predicted concentrations in each "compartment", and Q are the volumetric flow rates of blood throughout the body. Q and V are estimated from anatomical data.

The first-order, coupled differential equation system describing this model is formulated assuming a continuous time process.

$$\begin{aligned} V_v \frac{dC_v(t)}{dt} &= Q_c C_c(t) - Q_v C_v(t) \\ V_r \frac{dC_r(t)}{dt} &= Q_v C_v(t) + Q_s C_s(t) - Q_r C_r(t) \\ V_p \frac{dC_p(t)}{dt} &= Q_r C_r(t) - Q_r C_r(t) \\ V_L \frac{dC_L(t)}{dt} &= Q_P C_P(t) - Q_L C_L(t) \\ V_s \frac{dC_s(t)}{dt} &= Q_L C_L(t) - Q_L C_s(t) \end{aligned} \qquad \text{Equation (2)}$$

When converting the differential equation system into a state-space form, the rank of resulting state matrix (A) (see Equation (3)) is less than the order of the system. This rank deficiency manifests itself as a singularity when attempting to invert the matrix. This singularity is problematic if one wishes to produce a transfer function of the system (see Equation 4) to use (after discretizing) in parameter estimation, pole-placement, or control. The system must be discretized because the CT measurements are an intrinsic sampling process and the resulting signal enhancement curves reflect discrete time processes.

$$\vec{A} = \begin{pmatrix} \frac{-Q_V}{V_V} & 0 & 0 & 0 & 0 \\ \frac{Q_V}{V_R} & \frac{-Q_R}{V_V} & 0 & 0 & \boxed{\frac{Q_S}{V_R}} \\ 0 & \frac{Q_R}{V_P} & \frac{-Q_P}{V_P} & 0 & 0 \\ 0 & 0 & \frac{Q_P}{V_L} & \frac{-Q_L}{V_L} & 0 \\ 0 & 0 & 0 & \frac{Q_L}{V_S} & \frac{-Q_S}{V_S} \end{pmatrix} \qquad \text{Equation (3)}$$

$$\vec{B} = \begin{bmatrix} \frac{C_C}{V_C} \\ 0 \\ 0 \\ 0 \\ 0 \end{bmatrix} \quad \vec{C} = [0 \ \ 0 \ \ 0 \ \ 1 \ \ 0] \ \vec{D} = [0]$$

$$\hat{G}(s) = \vec{C}(s\vec{I} - \vec{A})\vec{B} + \vec{D} \qquad \text{Equation (4)}$$

Figure 5:
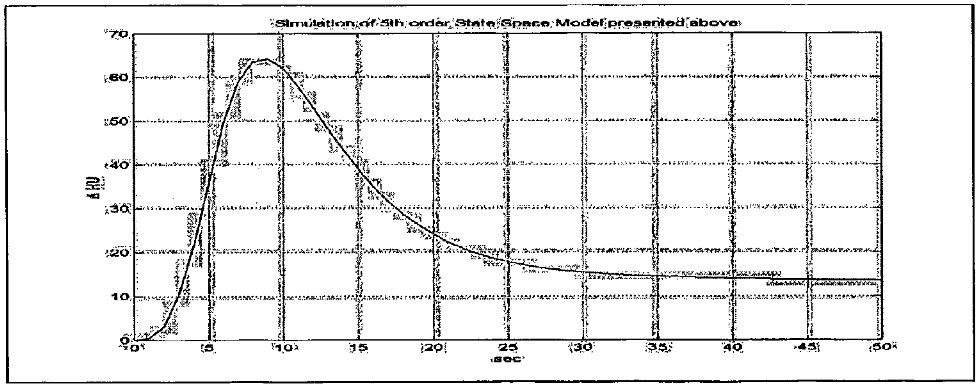
FIG. 5 illustrates a numerical solution of Equation (2), wherein the dynamics after 25 seconds approximates true recirculation phenomena.

Another problem with the reduced-order Bae model is that it doesn't capture the recirculation dynamics with a high degree of fidelity. Even though for CT angiography (CTA) applications we are interested in first pass dynamics, it would be useful to capture the recirculation peaks of contrast media resulting from recirculation through the systemic circulation and the myocardium. Comparison of the output of the Bae system with empirical data, as evidenced by the difference between FIG. 5 and FIG. 2C, shows a difference in the system time constant and the recirculation dynamics.

Figure 6:
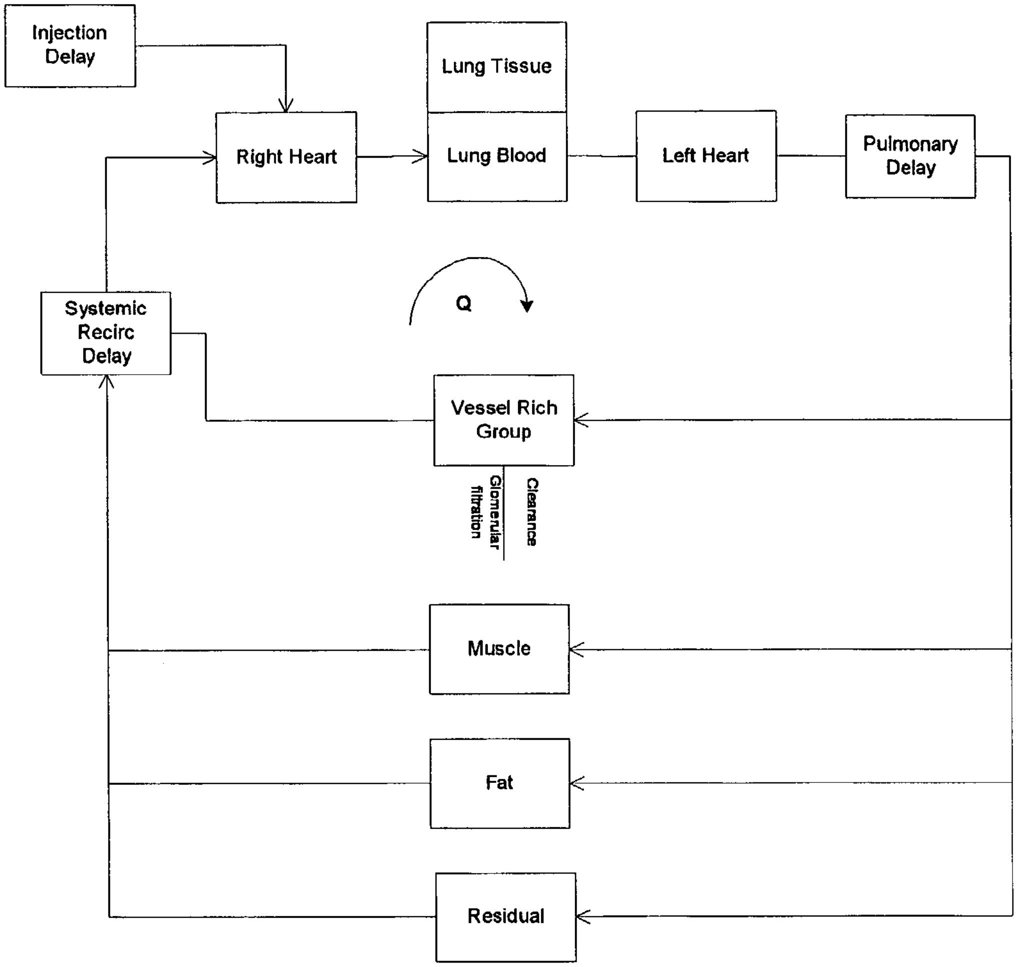
FIG. 6 illustrates a graphical depiction of a physiologic "hybrid" model describing the transport of drug through the cardiovascular system and pulmonary capillary-bed diffusion.

To overcome the mathematical difficulties intrinsic to the Bae modeling approach, a model adapted from that published by Wada and Ward was developed in the present invention. See Wada, D. R. and D. S. Ward (1994). "The hybrid model: a new pharmacokinetic model for computer-controlled infusion pumps." IEEE Trans Biomed Eng 41(2): 134-42, the disclosure of which is incorporated herein by reference. The model of Wada and Ward was developed to describe and control alfentanil (a strong analgesic) propagation within a patient (see FIG. 6). The Wada and Ward model allows for transformation into the discrete-time domain. That approach models delays in the drug dynamics (for example, propagation time of contrast through the pulmonary vasculature) by incorporation of explicit transport delays; as opposed to methodology of Bae et al. in which phase-lag is introduced by adding additional compartments. Each compartment in the model of FIG. 6 is formulated by applying a mass balance on the input and output of the compartment. Exogenous agent is introduced into the system via the infusion input. The mass flux of the infusion is added into the right heart compartment. The general mass balance equations for a compartment are given as:

Equation (5)

$$x_B^g = -\left(\frac{Q_{out}}{V_B} - k_{BT}\right)x_B + k_{TB}x_T + Q_{in}c_{in}$$

$$x_T^g = k_{BT}x_B - \left(\frac{Cl}{V_T} + k_{TB}\right)x_T$$

$$c_{out} = \frac{1}{V_B}x_B$$

Where the subscript B refers to the blood compartment and T refers to the tissue compartment of a 2 compartment, organ model. For single compartments, like blood vessels and heart chambers, Equation (5) reduces to one equation because the rate transfer terms, $k_{TB}$ and $k_{BT}$ are equal to zero. The k terms (or rate transfer terms or coefficients) describe the diffusion of the species across capillary membranes. The Cl term describes a clearance of the species from the compartment. In the case of X-Ray contrast that is excreted by glomerular filtration in the kidneys, the Cl term is associated with a compartment modeling the kidneys. $Q_{in}$ and $Q_{out}$ describe the volumetric flow rate of blood into and out of the compartment, and $C_x$ is the variable for the concentration of the species in the compartment of interest. This variable is of primary interest because the concentration of the contrast media is linearly related to the contrast enhancement in the vessel or organ.

In one embodiment, the algorithmic structure of the present invention assumes the blood volumes and cardiac output of the compartments in FIG. 6 can be approximated via, for example, look-up tables relating BMI, sex, and age to central blood volume and cardiac output. It is difficult to estimate a priori the k parameters describing the diffusion of the contrast out of the intravascular compartment. When attempting to describe contrast propagation for CTA imaging applications, we are primarily concerned with the "first pass" dynamics of the contrast media, the pulmonary system rate transition constants are those of most interest. In FIG. 6, therefore, the only 2-compartment element is that for the pulmonary circulation. One can, for example, start with estimates of these parameters based on published data, computer simulations, and/or population kinetic data. The intent of the algorithm is to derive an estimate of the pulmonary diffusion parameters via fitting of an empirical enhancement curve for the individual to the model. The fit of the k parameters may be done using a Simplex technique, such as Nelder-Mead algorithm, or system identification techniques (such as the Steiglitz-McBride approach). Once the identification phase is completed, an iterative, numerical optimization process can, for example, be used to determine an input protocol (given the constraints of the injection system—for example, no negative flow rates, a maximum flow rate of, for example, 6 ml/s, etc.) that will maximize the SNR of the image while minimizing the iodine load to the patient.

A simplification of the model in FIG. 6 combines the non-cardiopulmonary circuit components into a systemic blood block. This simplification is warranted when considering the first pass dynamics of contrast media for CTA applications, because the scan acquisition occurs during the seconds following contrast administration.

Figure 7:
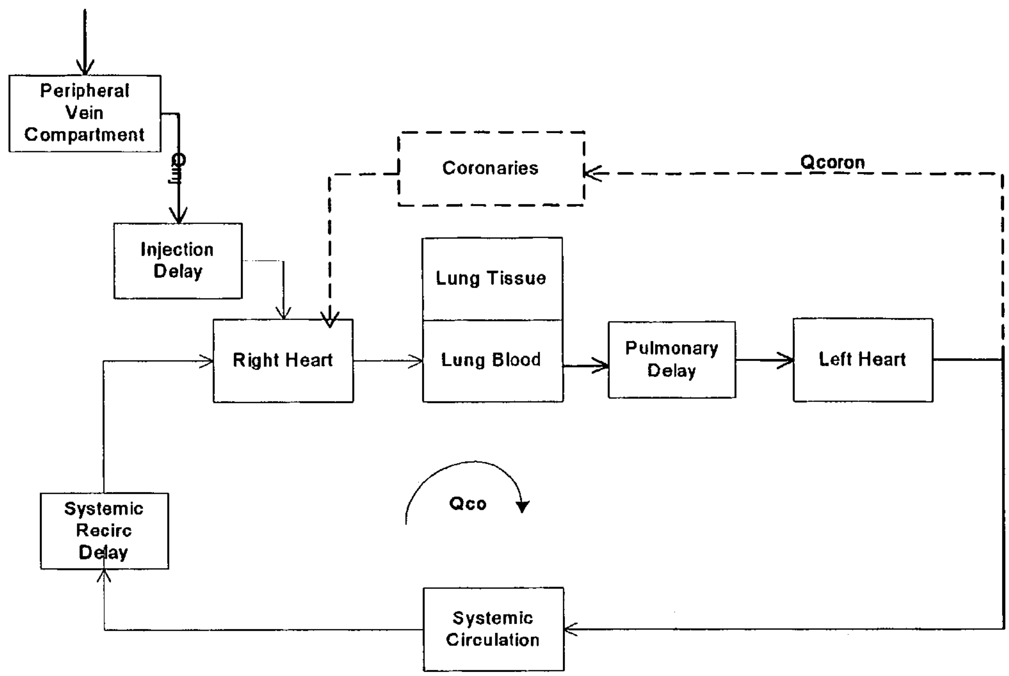
FIG. 7 illustrates a reduced-order model based upon the model of FIG. 6 in which Qco represents cardiac output.

FIG. 7 illustrates a graphical depiction of an embodiment of a reduced-order model of the present invention. The mass transfer relationship for each of the compartments is described by Equation (5). In FIG. 7, Qco represents cardiac output. The model in FIG. 7 can be used to describe the propagation of contrast within an individual patient. Assuming one knows the height, weight and sex of the patient, one can estimate the total, central blood volume (CBV) by:

Equation (6)

Male $$C\dot{B}V = (33.164 \cdot height^{725} \cdot weight^{425}) - 1229$$

Female $$C\tilde{B}V = (34.85 \cdot height^{725} \cdot weight^{425}) - 1954$$

Guytan, A. C., "Circulatory Physiology: cardiac output and regulation", Saunders, Philadelphia, p 173 ISBN: 07216436004. In Equation (6), height is in inches and weight is in pounds. One can also estimate the cardiac output using similar formulas, but that need not be done assuming that one can "test" the system with a small bolus of contrast medium. Static estimates of global circulatory parameters are, by nature, not likely to describe to a high order of fidelity the actual flow properties of a patient undergoing examination (for example, because of pathophysiology).

Because of the variability inherent in per-patient estimates, features of the test bolus enhancement can be used to better estimate the blood volume and cardiac output of the patient in the model of FIG. 7. This methodology reduces the number of unknown variables that are arrived at via parameter estimation. Mahnken et al. computed cardiac output estimates from individuals undergoing MDCT examination by analysis of the enhancement curves generated from small, test bolus administrations of contrast media. Mahnken, A. H., D. Henzler, et al. (2004). "Determination of cardiac output with multislice spiral computed tomography: a validation study." Invest Radiol 39(8): 451-4 and Mahnken, A. H., E. Klotz, et al. (2003). "Measurement of cardiac output from a test-bolus injection in multislice computed tomography." Eur Radiol 13(11): 2498-504, the disclosures of which are incorporated herein by reference. The approach taken by Mahnken et al. was earlier suggested by Garret and others. Garrett, J. S., P. Lanzer, et al. (1985). "Measurement of cardiac output by cine computed tomography." Am J Cardiol 56(10): 657-61, the disclosure of which is incorporated herein by reference. When an indicator is introduced to the circulatory system, the Stewart-Hamilton relationship states that the volumetric blood flow of the flow circuit is computed as:

$$Q_{CO} = \frac{M_I}{\int_0^{\infty} c(t)dt} \quad \text{Equation (7)}$$

where $M_I$ is the total mass of indicator (or tracer) injected to the circuit and c(t) is the measure of the indicator's concentration. For X-Ray contrast media, the values are the total mass of iodine injected to the patient and the concentration of contrast medium in mgI/ml units. Because of the known linear relationship between Hounsfield Units (CT attenuation number) and blood concentration of contrast medium (~25 HU/(1 mgI/ml) (see, for example, Bae, Heiken et al (1998) supra and Mahnken, Klotz et al. (2003) supra), one can integrate the time attenuation curve from the CT scanner to arrive at the term in the denominator of Equation (7).

Blomley, M. J. K. and Dawson, P., "Bolus Dynamics: Theoretical and Experimental Aspects," The Brit. J. of Radiology, 70 (1997), pp 351-359. present a geometric argument that allows one to estimate the blood volume from the injection site to the measurement site using the following relationship:

$$PeakEhn[HU] = \frac{Mass_I[\text{mg}]}{BloodVolume[\text{ml}]} \quad \text{Equation (8)}$$

where, again, $Mass_I$ or $M_I$ is the mass of iodine injected to the patient. PeakEnh is the peak value of intensity (arbitrary units, but for CT studies it is in HU) and BloodVolume is the volume of blood between the injection site and the recording site. To keep the units correct, one must convert the HU units to mgI/ml by dividing the PeakEnh by the scaling factor 25 [HU/(mgI/ml)]. Computation of Equation (8) allows one to estimate the blood volume in the cardiopulmonary circuit in FIG. 7. The difference between Equation (6) and Equation (8) gives the value of blood in the systemic circulation compartment. The blood volumes in the cardiopulmonary circuit (heart, lungs and peripheral injection compartment) are scaled based on anatomical data or estimated as below.

Differing from Fleischmann and Hittmair's approach of using a time enhancement curve recorded from one ROI placed over the descending aorta in axial, dynamic CT scans, in several embodiments of the present invention time enhancement curves are produced from the descending aorta and the pulmonary arteries. The two curves can be used to produce an estimate of the transit time through the pulmonary circulation and/or other cardiopulmonary parameters. Moreover, the issues associated with peripheral injection of contrast medium (such as backflow into side branch veins and other issues discussed below) will not affect the computation of the subsequent parameter estimation.

Figure 8:
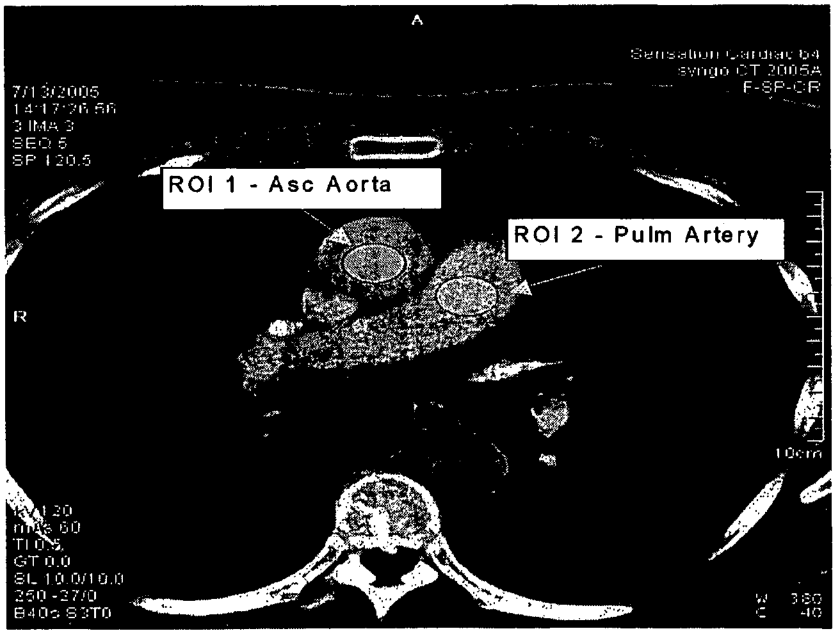
FIG. 8 illustrates an axial, dynamic CT image at the level of the pulmonary artery wherein two regions of interest (ROI) are encircled from which time enhancement curves are extracted.
Figure 9:
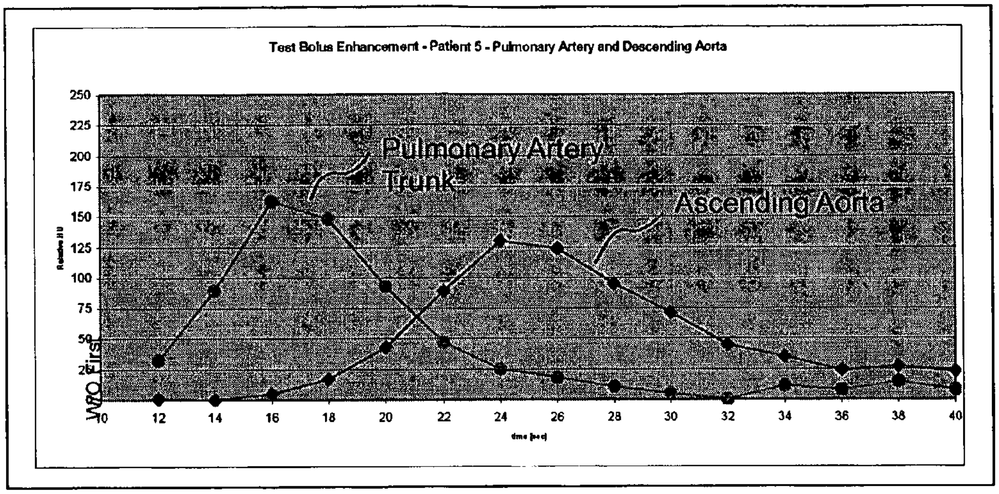
FIG. 9 illustrates dynamic CT, time-enhancement curves, after the administration of a 20 ml bolus of contrast medium with and without a saline push in a 239 lb 64 yr old female, wherein a first curve illustrates enhancement values in the pulmonary artery trunk, and wherein a second curve illustrates enhancement values from the ascending aorta.

FIG. 8 illustrates a typical axial CT image at a level that is scanned sequentially to generate the time enhancement curves in FIG. 9. In that regard, FIG. 9 illustrates dynamic CT, time-enhancement curves, after the administration of a 20 ml bolus of contrast medium with and without a saline push in a 239 lb 64 yr old female. A first curve in FIG. 9 illustrates enhancement values in the pulmonary artery trunk, and a second curve illustrates enhancement values from the ascending aorta. The pulmonary artery trunk enhancement is approximately that in the right ventricle (in that regard, contrast isn't much diluted from the RV to the PA). Because the contrast medium recirculates, the signals in FIG. 9 do not return to baseline, but rather are offset by an amount proportional to the residual contrast media in the blood stream. The recirculated contrast medium can result in overestimation of the cardiac output and blood volume estimates in Equation (8). To account for the recirculating contrast, one can fit the contrast enhancement curves from the test bolus to gamma functions of the form:

$$C(t) = k(t-t_0)^a e^{\frac{-(t-t_0)}{b}} \quad \text{Equation (9)}$$

where k, a and b are fit parameters. The fit can be done by a least squares technique. The resulting functions can then be used to derive parameter estimates of the cardiopulmonary system. The parameters to estimate are the transfer coefficients $k_{BT}$ and $k_{TB}$, $V_{RH}$, $V_{LH}$, $V_{Lung}$, and the transit delay $\tau$. These parameters can be lumped in a vector, $\theta(\theta=[k_{BT}, k_{TB}, V_{RH}, V_{LH}, V_{Lung}\ \tau])$. The measured enhancement profiles at the ROIs are $y_{PA}(n)$ and $y_{DA}(n)$. The ehancement at $y_{DA}(n)$ is a function of the enhancement in the pulmonary artery ($y_{PA}(n)$) and the parameter vector, $\theta-y_{DA}(\theta, y_{PA}(n),n)$. The goal of the parameter estimation is to produce an estimate of $\theta$ that optimally describes the patient data. Because there are many sources of variation and noise in the parameter estimates, it is reasonable to assume that the estimation errors will be Gaussian. Therefore, the Maximum Likelihood Estimation (MLE) can be used to derive parameter estimates with a cost function:

$$V = \frac{1}{2\sigma^2}\sum_{i=1}^{N}\left(y_{DA}^{meas}(n) - y_{DA}\left(\hat{\theta}, y_{PA}(n), n\right)\right)^2 \quad \text{Equation (10)}$$

where $\hat{\theta}$ is the estimated parameter vector. The best estimates of the parameter vector are defined as $$\hat{\theta} = \underset{\hat{\theta}}{\text{argmin}}\sum_{i=1}^{N}\left(y_{DA}^{meas}(n) - y_{DA}\left(\hat{\theta}, y_{PA}(n), n\right)^2 \quad \text{Equation (11)}$$

The variance of the parameter estimation vector is:

$$cov(\hat{\theta})=F^{-1} \quad \text{Equation (12)}$$

where F is the Fisher information matrix having eigen values that are proportional to the axes of V and that reflect the underlying uncertainty of the parameter estimates.

The minimization in Equation (11) can be done by the Levenberg-Marquardt algorithm or other numerical, optimization technique. The resulting parameter estimates are then used in generating predictive enhancements in the model of FIG. 7. To determine input functions that minimize the contrast medium while maximizing signal enhancement (while considering the constraints of the injection system), numerical, constrained optimization is done to determine the optimum contrast injection in FIG. 5.

B. Model-Independent Identification

In general, model independent algorithms are primarily data driven and do not require an a priori, parametric model of the system as set forth above. Model-independent identification using non-parametric spectral estimators and parametric modeling are described below.

Non-Parametric Spectral Estimators

Figure 10:
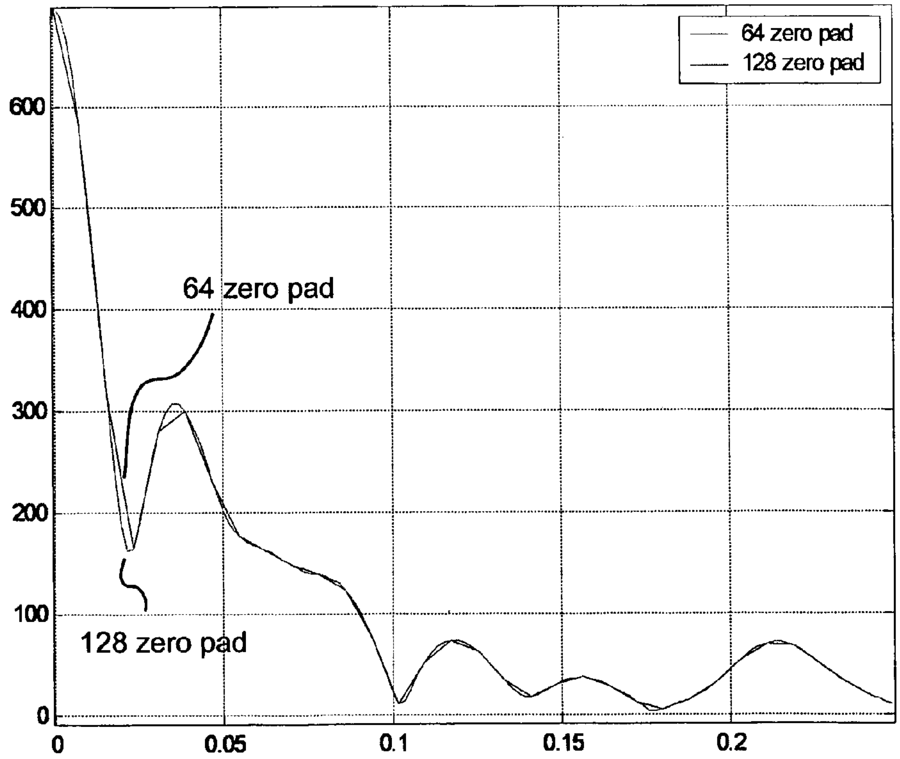
FIG. 10 illustrates a signal model used to produce numerator and denominator coefficients in Prony's method.
Figure 11:
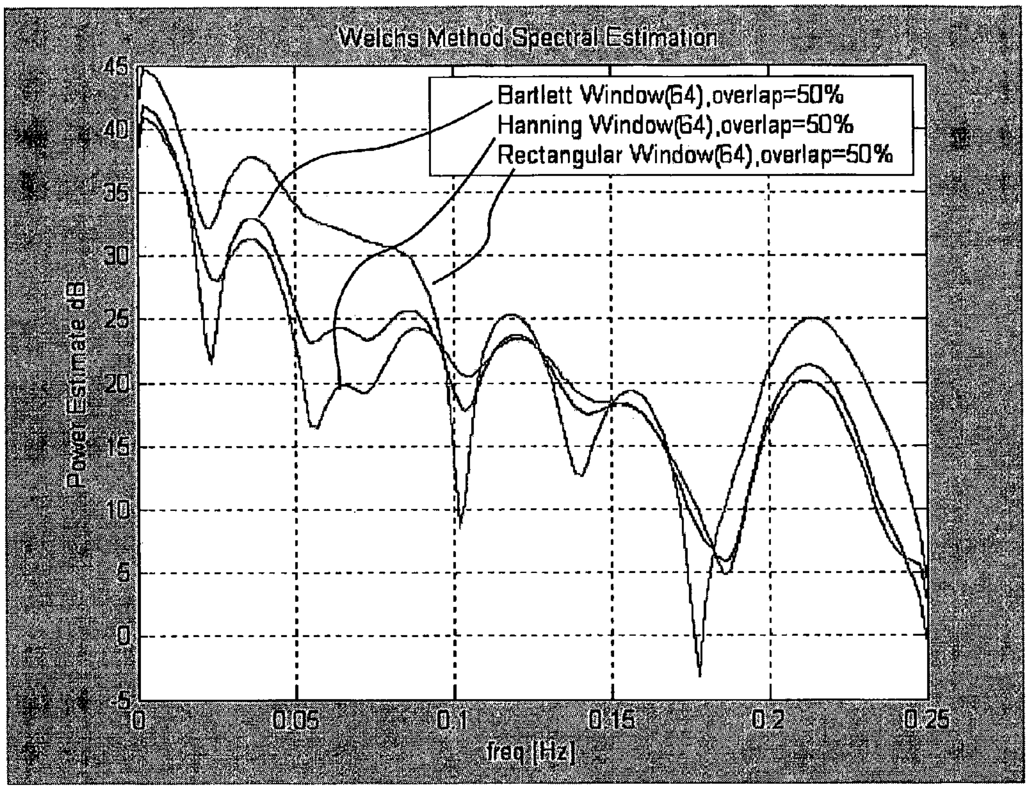
FIG. 11 illustrates a 64 point Fast Fourier Transform FFT taken of h(n) in Equation 1 (fs=0.5 Hz).

FIGS. 10 and 11 display the results of applying direct Fourier analysis (via a 64 order Fast Fourier Transform (FFT)) and Welch's Periodogram, respectively, to the patient impulse response function, $h_{test}(n)$. The periodogram of FIG. 10, in which a rectangular window was used, reveals that there is a pole close to DC. Also, there appear to be dominant poles at 0.22, 0.16, 0.12, and 0.03 Hz. In FIG. 10, the actual data vector had only 45 points. Both signals displayed were zero-padded—one to 64 points, the other to 128 points. There was no apparent improvement of resolution with a zero-padding of 128. As described above, there are 4 "poles" evident in the plot. The large DC component may be obscuring another pole close to 0 Hz. It is unclear whether the bump around 0.075 Hz is a pole. The temporal time-delay of the signal's primary peak is an important piece of physiologic information—a reason to model the zeros of the model.

Because the Welch Periodogram tends to have better resolution, has better variance properties, and has generally better spectral leakage characteristics than the periodogram, various Welch periodogram estimators were made to determine if a peak was present around 0.075 Hz, and to improve the resolution ("peakiness") of the other poles. Three results are illustrated in FIG. 11 as follows: (i) Bartlett's window (length=64) of the data vector with 50% overlap; (ii) a Hanning window (length=64) with 50% overlap; and (iii) a rectangular window (length=64) with 50% overlap. It is apparent that the Bartlett and Hanning windowed estimators reveal more detail. This is not surprising because these windows reduce spectral leakage that can confound true information hidden in the signal. An FFT of order 256 was used for the spectra of FIG. 11 to generate more data points and smoother estimates. It was found that FFTs of order greater than 256 did not improve the resolution meaningfully.

The Welch periodogram with a Bartlett window and 50% overlap illustrated in FIG. 11 reveals a pole near 0.075 Hz (and a smaller peak to the left of it). There are seven discernible poles in this estimate. The Bartlett window provides sufficient resolution and does not appear to attenuate the smaller poles (as compared to the Welch estimator with the Hanning window). It is apparent that the Welch method reveals more spectral structure of the underlying process.

Parametric Modeling

A method of estimating an appropriate, data based rational model is useful in understanding the appropriate assumptions to make regarding pharmacokinetics and pharmacodynamics. Moreover, an ARMA model can be useful in constructing control paradigms for the optimal delivery of contrast agent. FIGS. 10 and 11 display peaks and troughs, indicating that a more accurate model of the signal might include poles and zeros.

Figure 12:
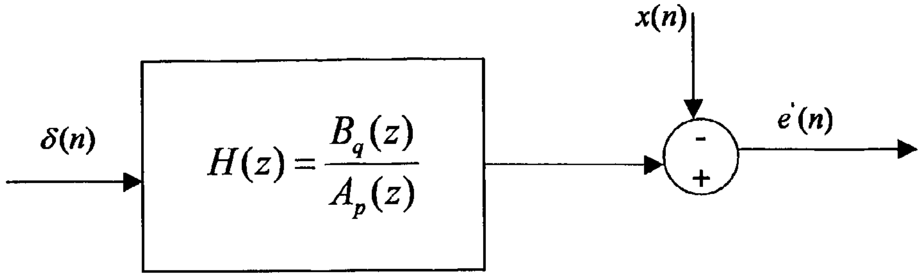
FIG. 12 illustrates Welch's method for spectral estimation—using h(n) as input.

Prony's method is an approach to estimating ARMA model coefficients of finite data records. See M. Hayes, *Statistical Digital Signal Processing and Modeling*. New York, N.Y.: Wiley and Sons, 1996, pp. 154-177, the disclosure of which is incorporated herein by reference. Prony's method assumes that the signal one wishes to model is an approximate impulse response of the system—depicted graphically in FIG. 12. See J. H. McClellan, "Parametric Signal Modeling," Chapter 1 in *Advanced Topics in Signal Processing*, Prentice-Hall, Englewood Cliffs, N.J., 1988, the disclosure of which is incorporated herein by reference. The algorithm iteratively solves for the best numerator and denominator coefficients, $a_p$ and $b_q$ in equation (14) (using Levinson-Durbin recursion) that minimizes, in a least squares sense, the output of the newly generated model with respect the input signal (the impulse response estimate), in equation (13).

$$\zeta_{LS} = \sum_{n=0}^{\infty} |e'(n)|^2 \quad \text{Equation (13)}$$

$$\frac{\partial \zeta_{LS}}{\partial a_p(k)} = 0 \quad \text{Equation (14)}$$

$$\frac{\partial \zeta_{LS}}{\partial b_q(k)} = 0$$

Another approach to pole-zero modeling of unknown systems is the Steiglitz-McBride method, also known as iterative prefiltering. An initial guess of the denominator coefficients in equation (1) is made using Prony's method. A least-squares minimization between the signal of interest and the previously estimated model of the signal is then performed and repeated iteratively for a number of iteration (as the error approaches zero). Whereas no general convergence property has been discovered for the Steiglitz-McBride method, the technique has been noted to converge within 10 iterations. See, for example, J. H. McClellan, "Parametric Signal Modeling," Chapter 1 in *Advanced Topics in Signal Processing*, Prentice-Hall, Englewood Cliffs, N.J., 1988. Additional detail of the Steiglitz-McBride method can be found in Hayes, *Statistical Digital Signal Processing and Modeling*. New York, N.Y.: Wiley and Sons, 1996, pp. 154-177, the disclosure of which is incorporated herein by reference.

Figure 13:
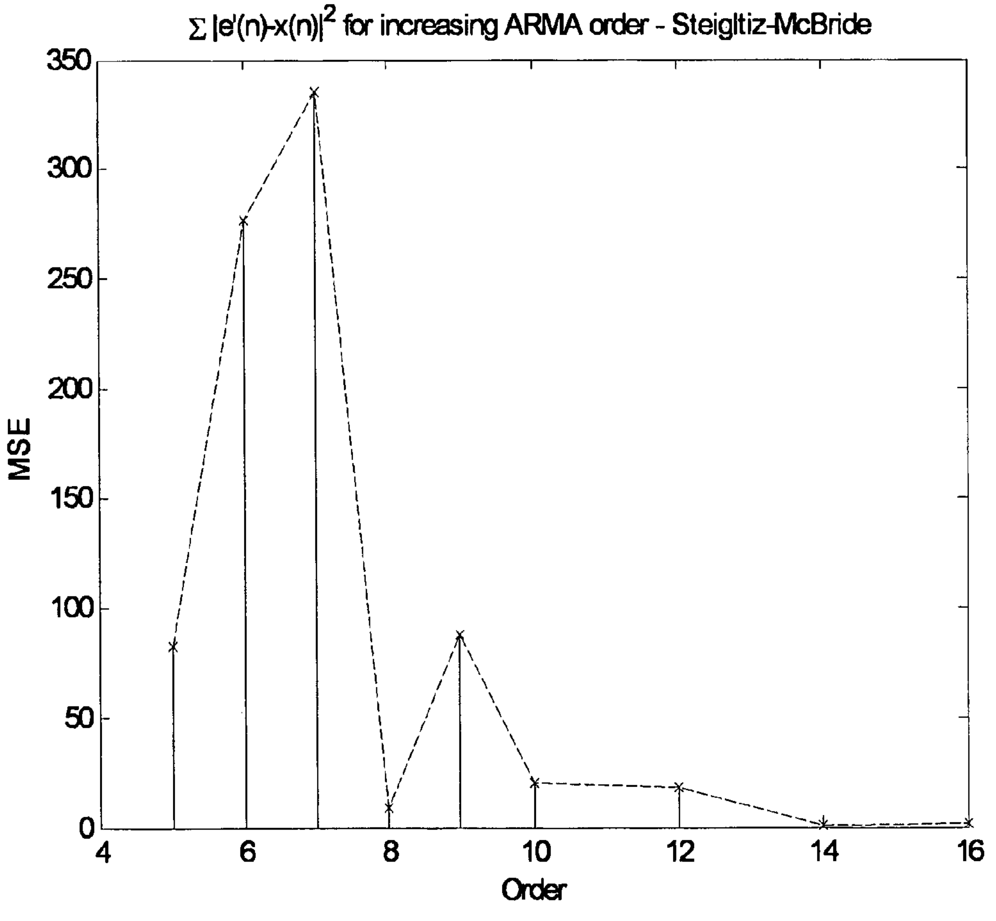
FIG. 13 illustrates a plot of the mean squared error between $h_{test}(n)$ and the impulse response derived from the Steiglitz-McBride estimate (run with 10 iterations) of the system for increasing order estimates.
Figure 14:
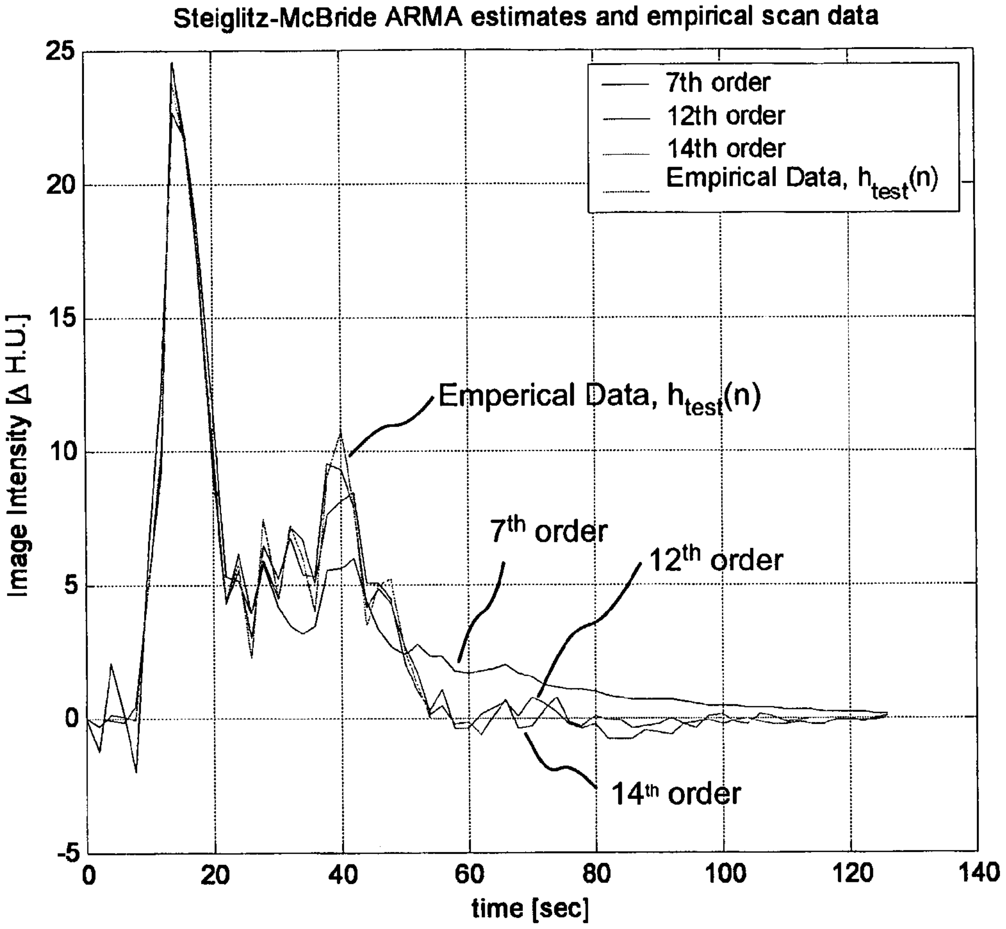
FIG. 14 illustrates a plot of the Steiglitz-McBride estimates of $h_{test}(n)$ for various orders of the transfer function.

FIG. 13 illustrates a plot of the Steiglitz-McBride's method (run with 10 iterations) spectral model estimate for various orders compared with the original signal. The Mean Squared Error (MSE) between the two signals drops below 25 for order 10 and higher, indicating that ARMA models with 10 or more terms in equation (6) represents the underlying dynamics sufficiently. FIG. 14 depicts the time series for varying order Steiglitz-McBride estimates of $h_{test}(n)$ compared to the impulse response data of FIG. 2*c*. It is apparent from the above results that the dynamics of a bolus of iodinated contrast medium may be described by spectral analysis techniques and modeled with ARMA signal modeling methods.

Once again, one or more physiological models as described above (or, for example, any of the ones proposed by Bae et al., or PHYSBE (a classic model of the human circulatory system available from The MathWorks, Inc. of Natick, Mass., and discussed, for example, on the internet at www.mathworks.com/products/demos/simulink/physbe in connection with the SIMULINK product available from The Mathworks, Inc.) can be a mathematical model employed in this invention. For example, one or more known external patient variables (for example height, weight, or blood pressure) can be entered into the model before the study is started to provide an initial estimate of the patient impulse response and thence the response to the imaging injection. Such an initial estimate can, for example, be used to identify or improve the structure for a parametric model or non-parametric model used to describe a response curve prior to performing a test injection.

In another embodiment, segments of the fluid path or the patient vasculature, for example the arm veins, can be modeled with MATLAB® available from The MathWorks, Inc., ASYS, available from ANSYS, Inc. of Canonsburg, Pa., r ALGOR, available from ALGOR, Inc. of Pittsburgh, Pa., or other applicable program.

Optionally the patient may be given a test injection and the measured response to the test injection is used to derive a measured patient impulse response. Physiological models can then be adjusted so that the predicted patient impulse response more closely matches the measured one. This methodology provides added confidence that customized imaging injection will produce the desired enhancement level course over time. Providing known external variables helps constrain the adjustments of the model to the patient, thus improving the fit of the model.

The improvement from the test injection information in the patient impulse estimation determined by the models of the present invention may be sufficient such that no further model modification is needed during the imaging injection, and the imaging injection proceeds as calculated from the beginning to the end of the injection. Or, in addition to the test injection modification, or in place of the test injection, during the imaging injection, the measured enhancement data from one or more regions of interest and/or other patient data such as, for example, heart rate, may be used to modify the model's prediction during the imaging injection. This modification can thence be used to determine a change in imaging injection protocols/parameters while the injection is being given, to better achieve the desired enhancement course over time in one or more regions of interest.

Patient parameters such as heart rate or respiration rate can change during a scanning procedure, for example, as a result of an increase in patient anxiety or discomfort. Retrieving heart rate or other information from the scanner or from an independent monitor and using such information to scale the injection can thus be advantageous.

In some medical procedures it is desirable to have different levels of enhancement in two or more regions of the body. An example is coronary artery visualization where is desirable to have high contrast in the coronary arteries and at the same time moderate contrast in the right heart (and to whatever extent possible in the left heart) so that both wall motion and artery lumen diameter can be visualized in one scan without artifacts from concentrated contrast streaming into the right heart. Furthermore, in liver scanning for cancer metastases, it can be desirable that the blood level of contrast be steadily increased, rather than constant at some level, so that tumors that are hyper vascular or hypo vascular can be seen as having enhanced or reduced contrast levels compared to normal lever tissue. The desired slope can be selected depending upon the type of cancer anticipated. In addition, for some liver imaging studies, it is desirable that the arterial blood levels of contrast be reduced during the later portal hepatic phase. This result is currently achieved by having a short imaging injection. However, because of patient differences, both contrast enhancement levels and timing of contrast arrival are not well controlled and can produce less than optimum images.

To achieve desired constant or time varying enhancement levels in multiple regions of interest, various analytical methods can be used if there is sufficient separation in time. However, if the desired enhancement levels over constrain the system, analytical approaches such as Fourier transforms or those mentioned elsewhere herein can run into difficulty. In such cases it can be desirable to use an optimizer or solver as known in the mathematical and computer arts. An example is to look at the mean squared error of the predicted enhancement from the desired enhancements over selected periods of time. This method has the benefit that the enhancement levels need to be defined only during the time of imaging, whereas some analytical approaches require that the enhancement level be defined for the entire study time, including rise and fall times.

An example of a solver that can be used is the Generalized Reduced Gradient (GRG2) nonlinear optimization code developed by Leon Lasdon, University of Texas at Austin, and Allan Waren, Cleveland State University. It is available in both Microsoft Excel and in MATLAB. It can be programmed or purchased for other languages as well.

A solver can also be provided with other constraints such as for example, a minimum flow rate, a maximum flow rate, a finite number of flow rate inflection points, a finite number of steady flow rates, or a maximum rate of change of flow rate. The constraints can be derived from injector operational limitations, patient safety limitation, or other practical or convenient limitations. It then determines the injection profile that best meets the desired contrast levels within the other constraints. A solver is especially suited for use with deconvolution and convolution approaches in the time domain. It can be used for instance to find the patient impulse response from the test injection and then to find the optimum injection profile using that patient impulse response and the desired enhancement level.

The devices, methods, and systems described herein are readily realized in a computer. Data input into the models of the devices, methods, and systems of the present invention can come for example from a human operator, from a hospital information system, from a scanner or imaging device, from an injector, and/or from one or more monitoring devices. Data optionally is provided (i) before the test injection, (ii) during and/or after the test injection, and/or (iii) during and/or after the imaging injection. Data can be automatically provided to the computer or entered by the human operator. Examples of outputs include timing and operating parameters for the imaging device or scanner and for the contrast injector. These outputs can optionally be automatically communicated among the respective devices, automatically communicated and confirmed or modified by the human operator, or read, confirmed or modified, and transferred by the human operator for entry into the appropriate devices. The automatic communications path can involve any of a number of custom or industry standard communications protocols. The manual path can include printing the injection or scanner parameters or protocol for accuracy and/or for record keeping. Communication between injectors, scanners and/or other equipment is discussed, for example, in U.S. Pat. No. 6,397,098, assigned to the assignee of the present invention, the disclosure of which is incorporated herein by reference. An example of a protocol suitable for use in the present invention is the Controller Automation Network (CAN) protocol described for example in ISO 11898. The imaging system of the imaging device (scanner) and injector can also communicate through the operator. In that regard, the imaging device can, for example, build the model and output the injection profile on a display device. The operator can then input the injection profile into the injector.

The algorithms and models of the devices, systems and methods of the present invention can, for example, be embodied in one or more computer programs implemented with one or more computers. Examples computer languages or environments suitable for use in the present invention include, but are not limited to, Excel, Visual Basic, Matlab, C++, and ACSL made by The Aegis Technologies Group of Huntsville, Ala. A computer implementing a program of the present invention can, for example, be a part of the imaging device, part of the injector, or an additional element in the imaging system. Alternatively, the operations can be distributed among computers associated with two or more devices.

Figure 15A:
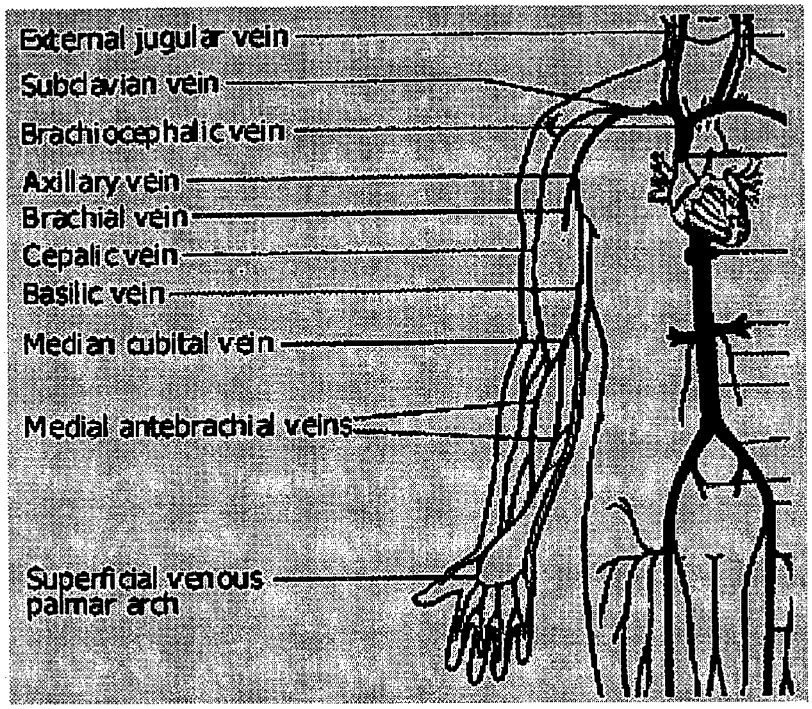
FIG. 15A illustrates a general diagram of the veins of the arm and those leading to the heart.
Figure 15B:
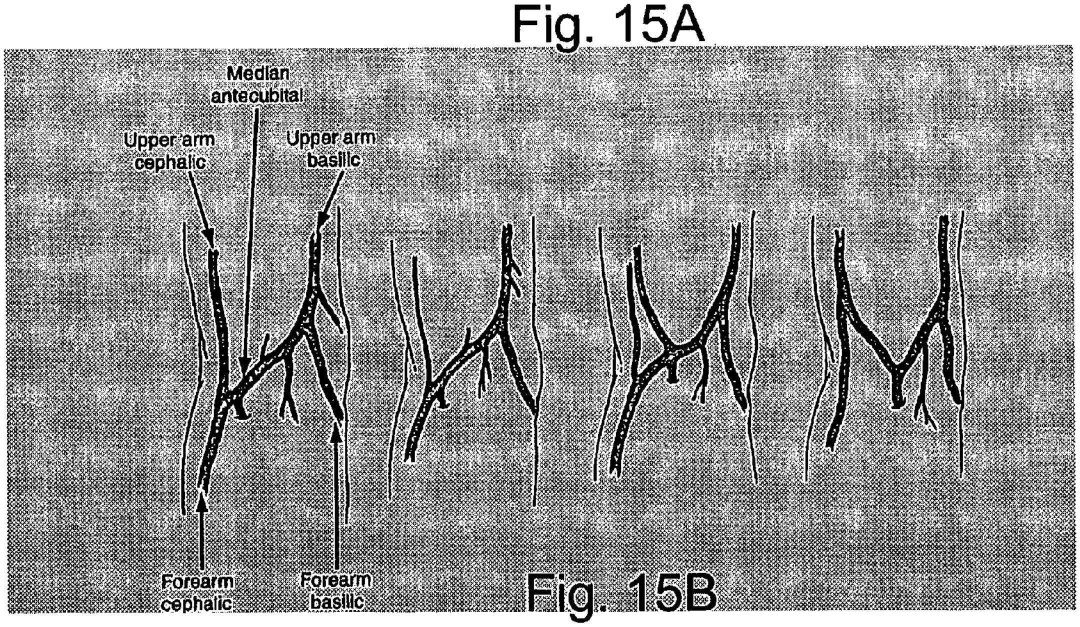
FIG. 15B illustrates several variations in arm vein anatomy.
Figure 16A:
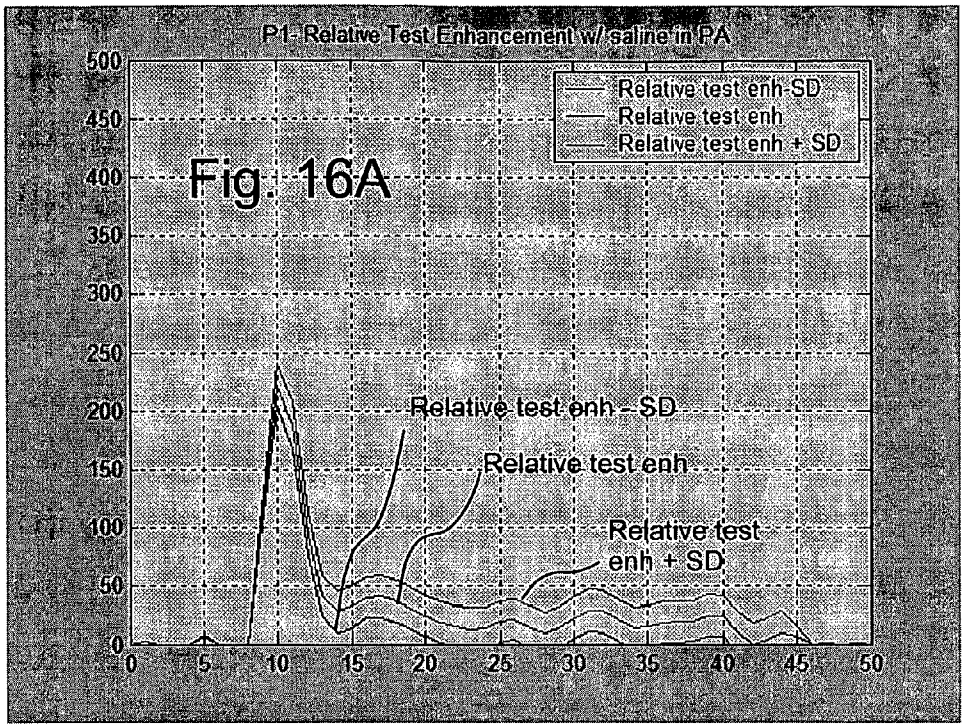
FIG. 16A illustrates relative test enhancement for a first patient in the pulmonary artery.
Figure 17A:
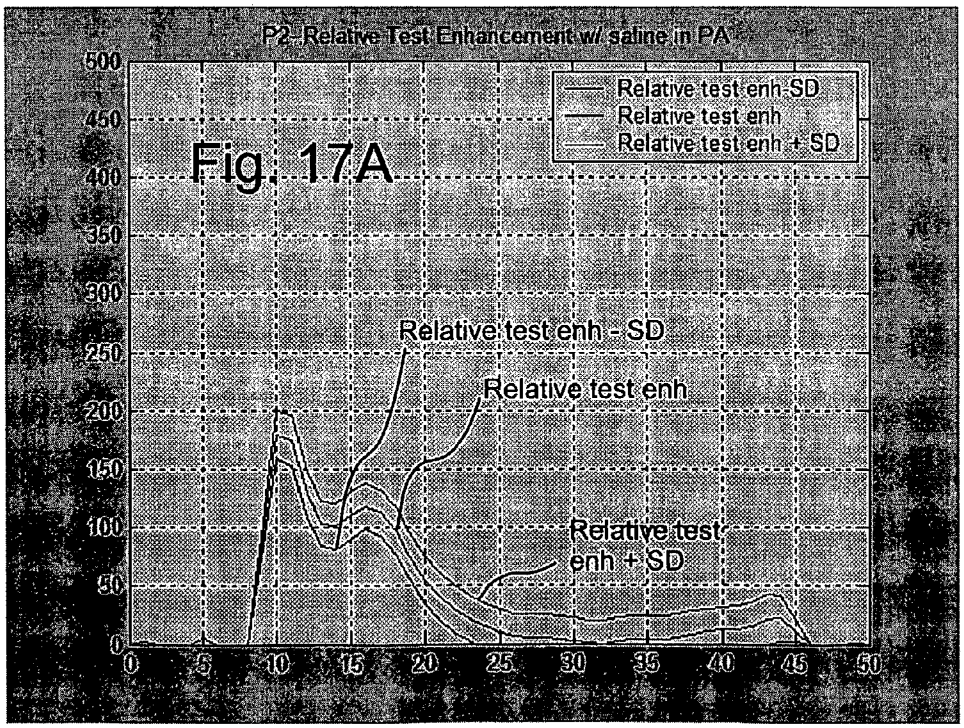
FIG. 17A illustrates relative test enhancement for a second patient in the pulmonary artery.
Figure 16B:
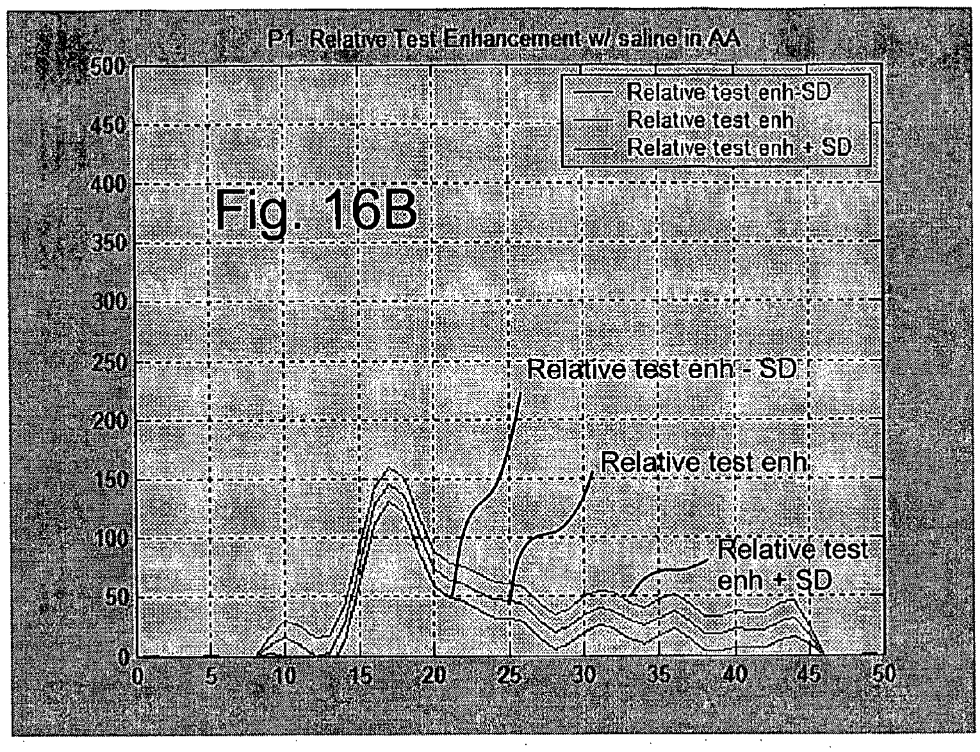
FIG. 16B illustrates relative test enhancement for the first patient in the ascending aorta.
Figure 17B:
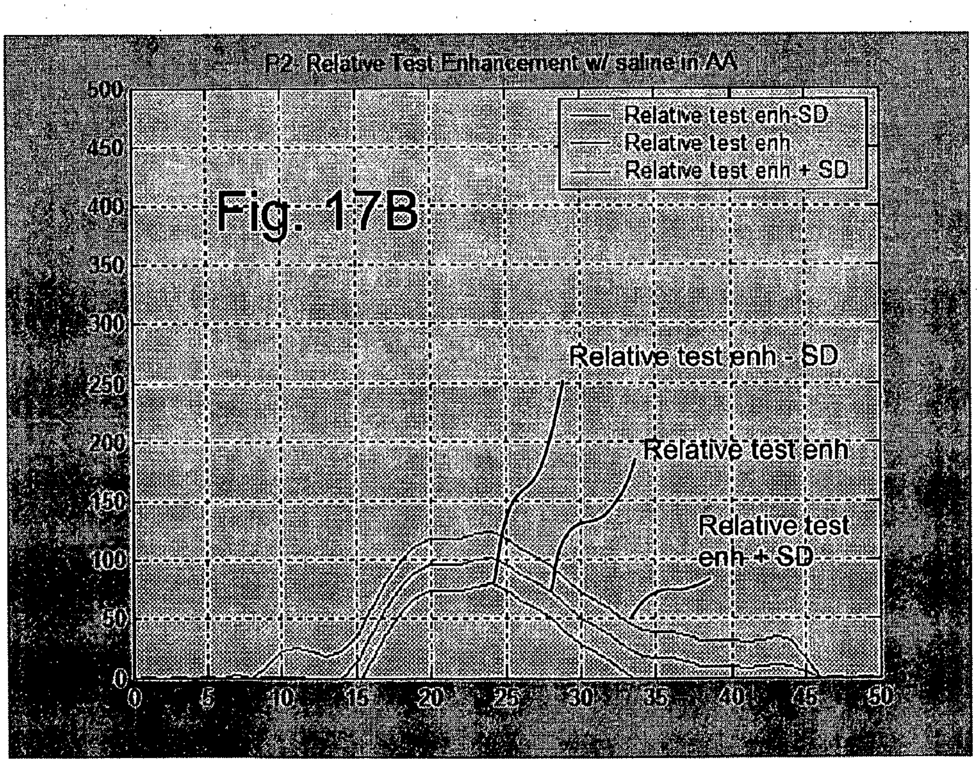
FIG. 17B illustrates relative test enhancement for the second patient in the ascending aorta.

FIG. 15A illustrates a general diagram of the veins of the arm and veins leading to the heart. FIG. 15B illustrates several variations in arm vein anatomy. It is apparent that fluid injected below the bifurcation can take more than one path to the heart. These paths can have very different lengths and resistances, resulting in different transit times. FIGS. 16A and 17A show pulmonary artery (PA) enhancement for two different patients after a test injection of 20 ml at 4.5 ml/s followed by at least 60 ml of saline also at 4.5 ml/s. The enhancement curve for Patient 1 in FIG. 16A shows a single peak, indicating that the contrast took a single path or multiple paths with similar travel times. The enhancement curve for Patient 2 in FIG. 17A shows two distinguishable peaks, as a result of contrast taking paths with different transit times. To account for this, an embodiment of a compartment model (as illustrated, for example, in FIG. 7) can include two parallel chambers with different volumes and different flow rates to allow for more accurate modeling of the curve of FIG. 17A. FIGS. 16B and 17B show ascending aorta (AA) enhancement curves for the same two patients. The dual peak for Patient 2 has been smoothed out by transit through the lungs. Thus if only AA measurements were taken, the ability to correctly model the arm flow would have been lost.

As described above, a number of the devices, systems, and/or methods described herein use a test injection to ascertain information about the patient's response to injection of a drug. For many models, a test injection can have any arbitrary profile, provided that that profile is known. For some drugs, the flow rates and volumes are low enough that the test injection does not perturb or modify the flow rate of blood in the vein. This means that the drug is quickly slowed down to the blood flow rate and is carried to the central vasculature at the speed of the blood flow. With X-ray contrast for imaging, the flow rates and volumes are often high enough, several milliliters per second, that significant perturbation does occur. In this case, once the injection of contrast is slowed or stopped, the contrast still traveling through the peripheral vasculature dissipates its momentum and slows down, because it is then only being pushed by the blood and the reduced contrast flow, if any. To overcome this, the test injection of contrast can be at a constant flow rate and be followed by several seconds of injection of a non-contrast enhancing fluid, for example saline, at the same flow rate to drive the contrast from the peripheral vasculature. FIGS. 18A and 18B show examples for two patients of the reduction in flow and total effective volume that occurs without the inclusion of a flushing fluid. The Injection Programmed flow is essentially what is achieved with the saline flush because all the contrast is pushed from the peripheral vasculature by the saline flush. For patient A, for the injection without the saline flush, the effective volume reaching the central vasculature was only 13.5 ml out of the injected 177 ml. Also, the injection started trailing off after only 3 seconds and dragged on until 13 seconds. For patient B, for the injection without the saline flush, the effective volume was 15 ml out of 17, but it never reached the actual flow rate. Thus an optimum test bolus can be defined as one with constant volumetric flow rate, wherein the concentration of the drug or active ingredient changes as programmed (for example a square pulse, a Gaussian shaped, or an arbitrary waveform) including several seconds of flow after the concentration of the active ingredient is zero.

In some instances it may be useful to do two or more test injections, one without a flushing fluid and one with a flushing fluid. Use of more than one test injection gives indication about extremity venous drainage that could be informative in determining the optimum imaging injection parameters.

Some patients have injection capable central venous catheters or PICC lines (peripherally inserted central catheter) so that the contrast does not have to flow through the branching extremity vasculature. This simplifies to some extent the modeling and should speed up contrast delivery in some instances. In these cases, the catheter can be explicitly modeled since its behavior is known. All embodiments of the present invention are suitable to operate with various injection sites, and some can accommodate test injections at one site and then imaging injections from a different site.

During the imaging injection, the rate of flow of contrast molecules (milligrams/S) can be affected in three ways. First, the volumetric flow rate (ml/S) of a constant concentration contrast can be varied. Second, the concentration of the active ingredients (number of contrast molecules, mg/ml) in the contrast can be changed while the volumetric flow rate in milliliters per second is kept constant. Third, both volumetric flow rate and concentration can be changed. The first option is achievable by a simple injection system just using a single fluid. This has the difficulty mentioned above that the flow of contrast already in the patient's arm may be reduced or increased as the incoming contrast flow is reduced or increased. Dilution of contrast at a constant flow is preferable to change in flow rate or velocities because it maintains the "driven flow" that has been or is being captured in the model or algorithm. This performance is possible with the drug injector of, for example, U.S. Pat. Nos. 5,840,026, 6,385,483 and 5,494,036, the disclosures of which are incorporated herein by reference. The STELLANT® injector, available from Medrad, Inc. of Pittsburgh, Pa., can, for example, be used to achieve high pressure high flow rates of both saline and contrast. The third option can be preferable in practice because it allows high flow rates, for example 6 to 10 ml/S, above the common 3-5 ml/S when needed. The third option also allows flow rate reduction down to the more moderate and somewhat safer flow rates. However, if the contrast flow needs to go below a lower limit, for example 3 ml/S, this result can be achieved via dilution to maintain the consistent driving of contrast out of the peripheral venous circulation.

By having an initially high flow rate reduced over time, the chance of an unnoticed extravasation is reduced. A nurse can, for example, palpate the injection site during the first few seconds. If an extravasation does not occur with the high initial flow, it is not likely to occur at lower flow rates. Alternatively, any extravasation detector is more sensitive to the faster signal rise from an extravasation at high flows and so is more likely to stop the injection should an extravasation occur.

An additional embodiment may utilize a concentric catheter including an inner or central lumen and an outer lumen such as that disclosed in connection with FIGS. 11A through 11C of U.S. patent application Ser. No. 10/821,210 (Published U.S. Patent Application No. 2004/025452), assigned to the assignee of the present invention, the disclosure of which is incorporated herein by reference. The two lumens of that catheter are arranged such that flow from the outer lumen substantially surrounds flow from the inner lumen. In cases where the imaging contrast is more viscous than blood or saline, the imaging contrast can be delivered through the center lumen and the saline or non-enhancing fluid can be delivered in the outer lumen. This helps reduce the pressure needed to push the contrast through the peripheral vein and into the central venous system. As mentioned herein, the contrast and non-contrast flows can be adjusted if desired to maintain a constant volumetric flow through the peripheral vessels as the rate of contrast molecule delivery varies. This concentric catheter can also beneficially be connected to a PICC line or central catheter lines via a luer adapter to provide a flow of contrast inside a flow of saline, which reduces the pressure drop in the PICC or central catheter line.

If the test injection includes injection of a non-enhancing fluid at its end, then the injector must "remember" and account for the fact that any applicable connector tubing and central catheter will be filled with non-contrast enhancing fluid. Similarly, when the injector is first prepared for the patient, the connector tubing between the injector and the patient may be filled with contrast or saline and the injector needs to account for this. Otherwise there will be an unexpectedly early or later arrival of contrast and the resulting impulse response or model adaptation will be inaccurate. Not accounting for this can be especially problematic in algorithms that adaptively respond during the imaging injection.

It is desirable that the image intensity data be reasonably accurate and repeatable. However, many things can affect the absolute accuracy of image reconstruction algorithm and process that produces a 2D image in Hounsfield units. For example KV (kilovoltage on the tube), FOV (field of view), table height, and reconstruction algorithms are known variables affecting precision in CT. Thus it is desirable that a consistent reconstruction algorithm and other set of variables be used. However, with modern scanners, there are a number of automatic dose reduction approaches that cause the imaging variables to change during the scan. Moreover, with ECG gating, the reconstruction algorithm can change from slice to slice. Once approach to overcome this variability can be adapted from quantitative CT (QCT). A bone mineral standard or calibration phantom is placed in the scanner with the patient as illustrated in GE Lunar Corp brochure SL172E 7/01 copyright 2001, the disclosure of which is incorporated herein by reference. This approach allows translation of reconstructed Hounsfield units to absolute Hounsfield units. A second approach is to use fat, bone and/or muscle tissue of the patient, rather than external regions of interest in the calibration standard. This approach will only work in some instances, because the tissues are of constant Hounsfield units only until the contrast beings to reach that tissue. For example, it is likely to work where the imaging target or region of interest is the lungs, heart, or great vessels and tissues such as the spine and esophagus are used. This use of the patient's tissue for calibration is also more applicable to a test injection or the beginning of an imaging injection than to the mid or later parts of an imaging injection.

The QCT standard can, for example, be built into or be a part of the patient support table, the cushion on the table, and or the scanner gantry. It does not have to be a specific phantom structure, for instance aluminum, carbon epoxy, and foam often used in constructing the patient couch would suffice if they are of consistent X-ray attenuation. In these cases where the standard is always in a specific place on an image, the reconstruction algorithms can automatically access the standard values and correct the patient image. The QCT standard can also be in a region that is never shown on the patient image.

It is desirable that the image intensity data be reasonably accurate and repeatable. However, many things can affect the absolute accuracy of an image reconstruction algorithm and process that produces a 2D image in Hounsfield units. For example KV (kilovoltage on the tube), FOV (field of view), table height, and reconstruction algorithms are known variables affecting precision in CT. Thus it is desirable that a consistent reconstruction algorithm and other set of variables be used. However, with modern scanners, there are a number of automatic dose reduction approaches that cause the imaging variables to change during the scan. Moreover, with ECG gating, the reconstruction algorithm can change from slice to slice. One approach to overcome this variability can be adapted from quantitative CT (QCT). A bone mineral standard or calibration phantom is placed in the scanner with the patient as illustrated in GE Lunar Corp brochure SL172E 7/01 copyright 2001, the disclosure of which is incorporated herein by reference. This approach allows translation of reconstructed Hounsfield units to absolute Hounsfield units. A second approach is to use fat, bone and/or muscle tissue of the patient, rather than external regions of interest in the calibration standard. This approach will only work in some instances, because the tissues are of constant Hounsfield units only until the contrast beings to reach that tissue. For example, it is likely to work where the imaging target or region of interest is the lungs, heart, or great vessels and tissues such as the spine and esophagus are used. This use of the patient's tissue for calibration is also more applicable to a test injection or the beginning of an imaging injection than to the mid or later parts of an imaging injection.

Another approach for improving accuracy is to fit the model to successive regions of interest. In one CT slice it is possible to image several distinct regions, for example the left heart, lung tissue, the right heart, and the descending aorta. If the model is fit to the Hounsfield unit enhancement as the contrast flows through the various regions, a more accurate fit can be achieved as was mentioned above in relation to FIGS. 16A through 17B. This may potentially be most effectively applied to physiologically based models because the model is generally readily separable and provides access to the predicted enhancement for physiologically distinguishable regions of interest.

Several of the embodiments of the present invention discussed herein have primarily related to the achievement of a desired image contrast patient response in Hounsfield units. Examples of desired image contrast patient responses are a relatively constant or flat enhancement, as is sometimes desired for blood vessel imaging, a continuously rising blood contrast level, as, would be useful for liver metastatic cancer detection, and a rising and then falling contrast level to allow portal venous phase liver imaging. However, the present invention facilitates achievement of generally any arbitrary enhancement profile that may be required by a doctor to make a diagnosis, such as for functional imaging or perfusion mapping.

In addition the enhancement occurs over a specific range of time. Because of the way the analysis is conducted, the zero of time is arbitrary. In one embodiment, the desired enhancement is defined at a time far enough from 0 that the injection will not need to start until well after 0 time. For example, the enhancement can be selected to reach the desired plateau at 100 seconds. Then, once the model is optimized or constructed for the patient, the model will predict the start time for the imaging injection, for example 70 seconds. In use, it is the difference between the start of the injection and the start of the desire enhancement that is used to determine the scan delay, in this example 30 seconds. Once everything is ready, the injector is started (from the injector, scanner, or a third piece of equipment) and then the scanner begins executing the programmed series of scans 30 seconds later (again triggered by the injector, scanner, or third piece of equipment).

Figure 19A:
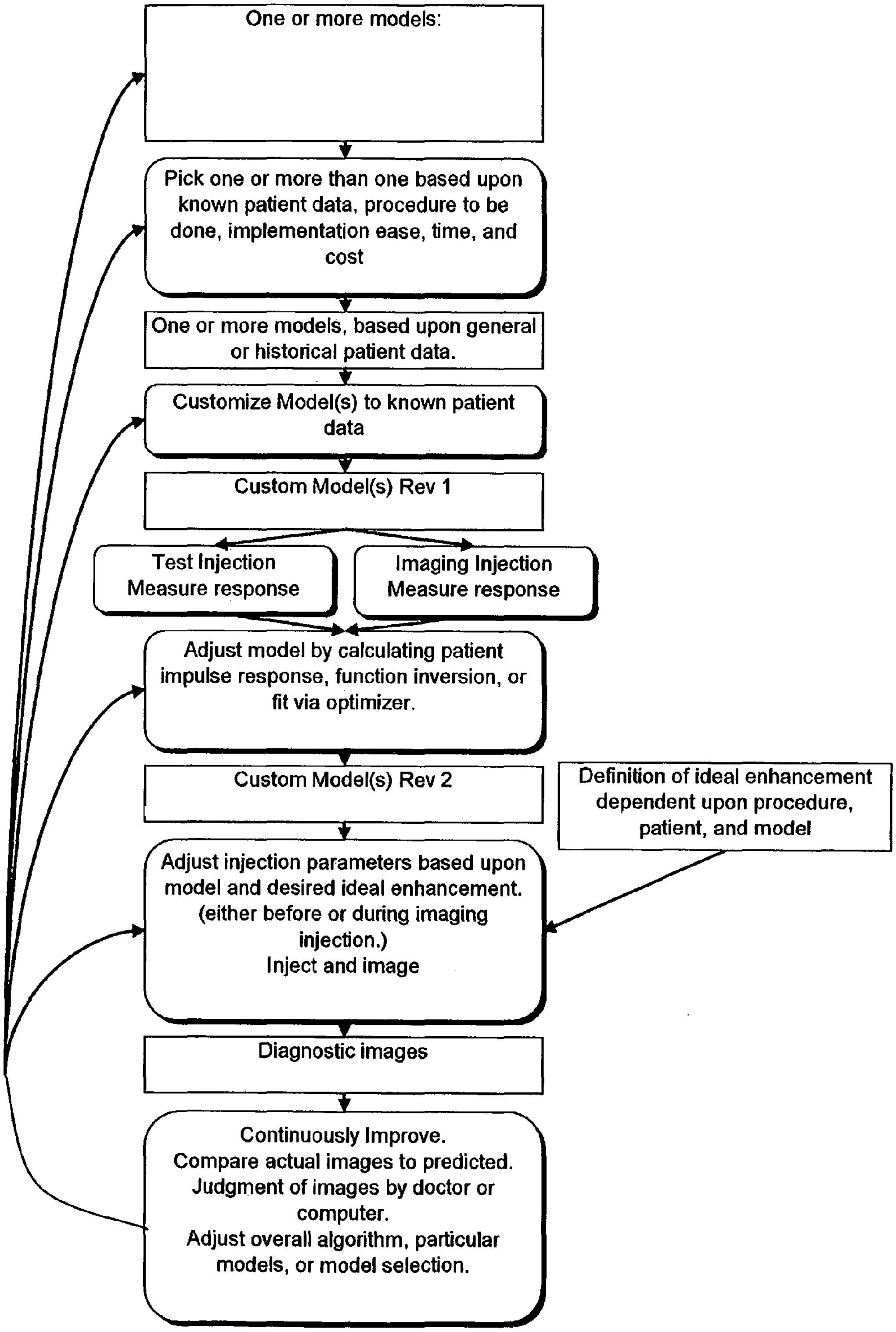
FIG. 19A illustrates a flowchart of a generalized method of the present invention.
Figure 19B:
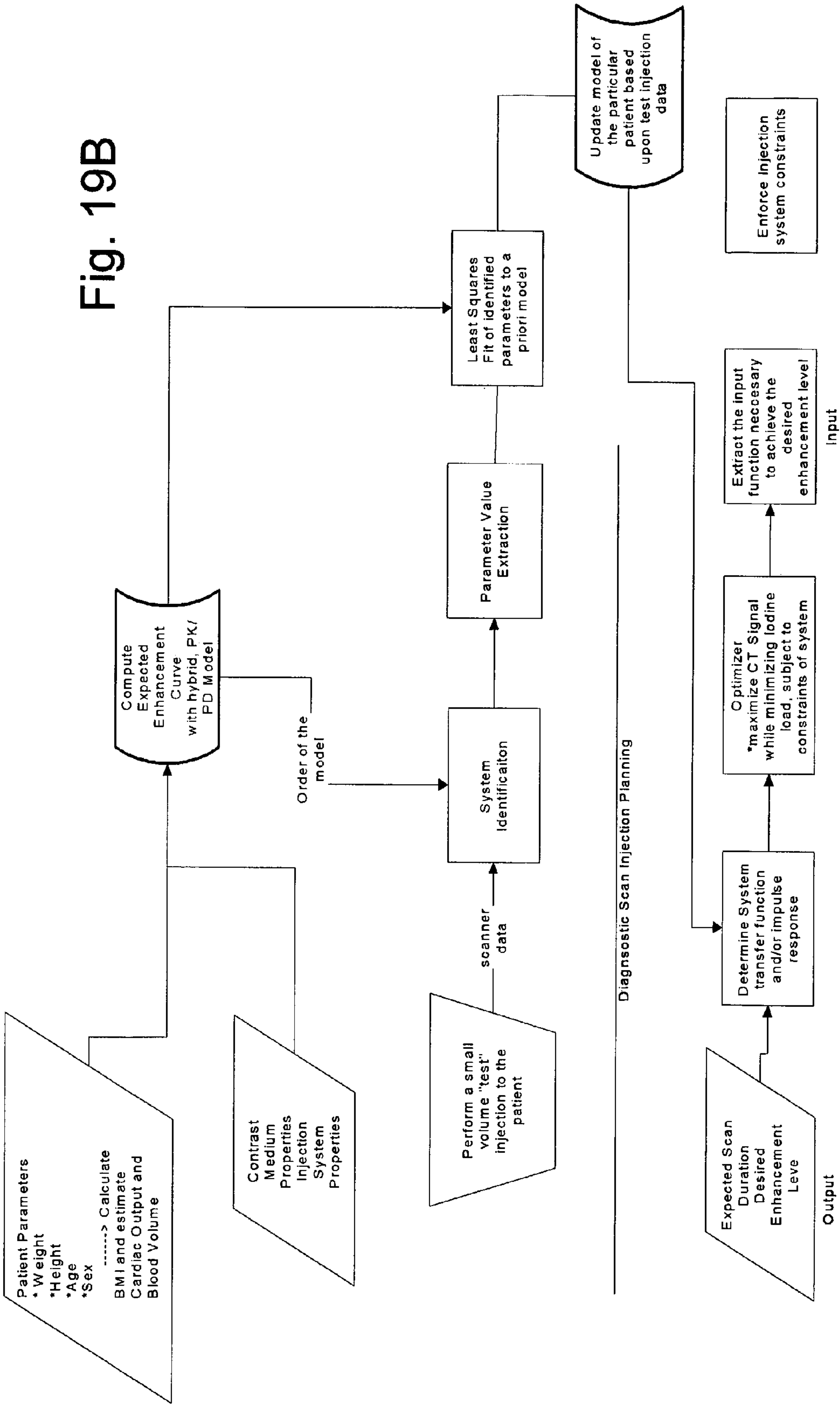
FIG. 19B illustrates a flow chart of an embodiment of a method of the present invention incorporating, for example, the model of FIG. 7.

Many of the embodiments of this invention are discussed in relation to adjustments, modifications, or updates of the model for a patient being made based upon test injection imaging or image injection imaging (see, for example, FIGS. 19A and 19B). In addition, the general or multi-patient model can be adjusted, modified, or updated based upon results of one or more patients for use with other patients. This is especially applicable if the embodiment being implemented does not use a test injection or real time adjustment of injection parameters. In this case the patient specific parameters used all are known before starting the imaging and could include for example disease state, height, weight, approximate cardiac output (normal, poor, failing) and other generally knowable parameters.

The representative embodiments of the present invention have been discussed primarily in relation to the various embodiments of CT imaging. However, one skilled in the art appreciates that the devices, systems and methods of the present invention can be readily used (with or without modification) to enable improved optimum dosing in all other imaging devices and methods, including, for example, magnetic resonance imaging, ultrasound imaging, X-ray fluoroscopy, positron emission tomography, and various light imaging devices. Any modifications of the present invention for use in imaging procedures other than CT imaging are well within the skill of those in the art.

Various drugs can benefit from application, of this invention. These include, but are not limited to, ionic, non-ionic, dimeric, and blood pool contrast agents. Also included are physiological active drugs, especially those with short half-lives. Two or more different or similar models can be used with two or more different drugs during the same diagnostic procedure, such as imaging contrast for CT, MR, or ultrasound in combination with dobutamine for cardiac stress imaging.

Imaging and image enhancement levels are examples of output from a “sensor”. Other sensors suitable for use in the present invention are listed, for example, in U.S. Pat. Nos. 5,840,026 and 6,385,483, the disclosures of which are incorporated herein by reference. Still other sensors relate to other physiological parameters such as blood level of a drug (for example, a chemotherapy drug) or, blood level of a resultant of the drug (for example, blood glucose or dissolved blood clot molecules). Other examples of sensors suitable for use in the present invention include, but are not limited to, EEG (Electroencephalogram), muscle response sensors, or specific nerve bundle activation level sensors.)

In some imaging devices, the goal is to maintain constant enhancement levels over longer times than a few seconds. One example is ultrasound imaging. These contrast drugs are normally blood pool agents, meaning that they stay in the blood vessels and do not diffuse into the extravascular or intracellular spaces. Thus the derived mathematical model will be different in detail than mathematical models derived for use in CT, but the devices, systems and methods disclosed herein are similarly useful and applicable.

When a model is developed for a patient, it can be recorded and saved, so that it becomes the basis for a subsequent model. This can eliminate some time for subsequent tests, for example it could eliminate the need for a test injection. Moreover, it can increase the accuracy of the model. In addition, recording and saving test scan measurements or images can help in model creation for a future scan.

Given that a model/patient transfer function is identified (for example, having the form of Equation (1)), one may attempt to solve for an input signal that will produce a desired output (that is, a desired level of contrast enhancement in an anatomical region of interest). Assuming a Linear Time Invariant system (that is also causal and stable), the input-output relationship of a discrete-time (or sampled) system is:

$$y(n) = \hat{h}(n) * x(n) = \mathfrak{F}^{-1}\{H(z)\} \cdot x(n) = \sum_{m=0}^{n} x(m)\hat{h}(n-m) \quad \text{Equation (15)}$$

where the operator $\mathfrak{F}^{-1}\{\bullet\}$ is an inverse, discrete Fourier transform. Because the system is assumed to be linear, time invariant, and causal the terms within the summation on the right hand side can be interchanged so that the input-output relationship can also be written as:

$$y(n) = \sum_{m=0}^{n} \hat{h}(m)x(n-m) \quad \text{Equation 16}$$

The H(z) term can be computed by a priori modeling of the patient/drug system as described above, computed by system identification techniques operating on data collected during a brief inquiry of the system with a small injection of pharmaceutical, or computed with a combination of both approaches. Assuming a noise free measurement, Equation 15 can be recast into a linear algebra formulation:

$$\vec{y} = \overline{\overline{H}} \cdot \vec{x} \quad \text{Equation (17)}$$

where $\vec{y}$ is an Mx1 length column vector, $\vec{x}$ is a column vector of values describing the input to the system response of the identified model of length N (assume that M=N). The matrix $\overline{\overline{H}}$ is a lower triangular, Toeplitz matrix having structure:

$$\overline{\overline{H}} = \begin{bmatrix} \hat{h}(1) & 0 & 0 & 0 \\ \hat{h}(2) & \hat{h}(1) & 0 & 0 \\ M & \hat{h}(2) & \hat{h}(1) & 0 \\ \hat{h}(M) & \hat{h}(M-1) & L & \hat{h}(1) \end{bmatrix} \quad \text{Equation (18)}$$

One approach to solving Equation (17) for the vector $\vec{x}$ (input) given a desired output ($\vec{y}$ vector) and a Toeplitz matrix $\overline{\overline{H}}$ as expressed in the form of Equation (18), is to find the a vector x that minimizes the cost function (known as a linear least-squares problem):

$$J(\bar{x}) = \frac{1}{2}\left\|\bar{y} - \overline{\overline{H}}\bar{x}\right\|^2 = \frac{1}{2}\left(\bar{y} - \overline{\overline{H}}\bar{x}\right)^T\left(\bar{y} - \overline{\overline{H}}\bar{x}\right) \quad \text{Equation (19)}$$

The cost function in Equation (19) achieves its global minimum when its gradient equals zero. A well known result is that the vector x can be solved as:

$$\bar{x} = \left(\overline{\overline{H}}^T\overline{\overline{H}}\right)^{-1}\overline{\overline{H}}^T\bar{y} = \overline{\overline{H}}^+\bar{y} \quad \text{Equation (20)}$$

where $\overline{\overline{H^+}}$ is the Moore-Penrose pseudo-inverse. Equation (20) is the general solution to the overdetermined case when the row rank of H exceeds the column rank. When the row and column rank of $\overline{\overline{H}}$ are equal (and thus a square matrix), the solution of Equation (19) is:

$$\bar{x} = \overline{\overline{H}}^{-1}\bar{y} \quad \text{Equation (21)}$$

where the inversion of H may be computed via a number of techniques (Gauss elimination with pivoting, singular value decomposition, etc.). Clearly, if the matrix of the model's impulse response $\overline{\overline{H}}$ is not invertible (due to singularities or being ill conditioned due to noise), then one is unable to determine a reliable input signal that can achieve a desired output. This is an intuitively satisfying condition because if the system of Equation 1 is not invertible then the conditions of linearity, time invariance, and causality have not been enforced (or the true process can not be approximated with those assumptions). It is notable that significant noise and/or model uncertainty can cause great deviations in the numerical result of Equation (21).

A constrained deconvolution solution (a regularization deconvolution formulated as a constrained optimization problem) in which the form of the expression to minimize (DeNicolao G. 1997) is set forth as:

$$\min_{u \geq 0} (y - Hu)^T B^{-1} (y - Hu) + \gamma u^T F^T F u \qquad \text{Equation (21)}$$

can also be used. Equation (21) does not have a closed-form solution so it must be solved via iterative techniques. The H matrix is a lower diagonal, Toeplitz matrix of impulse coefficients—which can be determined via a system identification method, or by simply inserting the values of the time-enhancement curve imaged from a test injection. The y term represents the desired output and u is the control. The second term in Equation 21 represents a means for addressing the noise corruption and uncertainty in the measurement. The matrix F represents a "forgetting" factor that can have on its diagonal the covariance estimate of the noise. Equation (21) can, for example, be solved using a weighted least-squared numerical optimization and/or multi-objective constrained optimization techniques.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. A method of controlling an injector system for delivering a contrast enhancing fluid to a patient, comprising:
- (a) determining at least one patient transfer function for the patient based upon data specific to the patient, the at least one patient transfer function providing a time enhancement output for a given input, the data specific to the patient including at least one of an estimate of physiological parameters of the patient, an estimate of anatomic parameters of the patient and an enhancement caused by an injection of the contrast enhancing fluid into the patient;
- (b) determining a desired time enhancement output;
- (c) using the at least one patient transfer function to determine an injection procedure input; and
- (d) controlling the injector system at least in part on the basis of the determined injection procedure input.

2. The method of claim 1 wherein the contrast enhancing fluid is a CT contrast enhancing fluid, a MRI contrast enhancing fluid, an ultrasound enhancing imaging fluid or a radioactive contrast enhancing fluid.

3. The method of claim 1 wherein at least two patient transfer functions are determined and the injection procedure input is determined on the basis of one of the patient transfer functions.

4. The method of claim 3 wherein a first patient transfer function is determined using a system identification model comprising parameters related to physiological parameters of the patient and a second patient transfer function is determined using a mathematical model determined by collecting data corresponding to a time enhancement curve resulting from an injection, the mathematical model describing the data.

5. The method of claim 3 wherein a determination is made as to which patient transfer function provides a best correlation between a given input and a resulting output.

6. The method of claim 1 wherein the injection procedure input is determined considering at least one operational limitation or constraint of the injector system.

7. The method of claim 6 wherein the at least one patient transfer function is determined by the steps of:
- (a) collecting data corresponding to a time response curve resulting from an injection of the fluid; and
- (b) determining at least one mathematical model describing the data.

8. The method of claim 7 wherein the mathematical model is not determined by a continuous or a discrete-time Fourier transform of the data.

9. The method of claim 7 wherein the model is a parametric model.

10. The method of claim 9 wherein the model is a moving average or an autoregressive moving average.

11. The method of claim 9 wherein the mathematical model assumes linearity and time invariance.

12. The method of claim 7 wherein the model is a non-parametric model determined by a spectral estimation technique.

13. The method of claim 12 wherein the spectral estimation technique is Welch's method, Bartlett's method, a multiple signal classification (MUSIC) method, or a Periodogram method.

14. The method of claim 7 wherein data is collected during at least one test injection prior to an imaging injection.

15. The method of claim 7 wherein the at least one patient transfer function is updated with data collected during an imaging injection.

16. The method of claim 6 wherein the injection procedure input is determined using an analytical solution or using a numerical, constrained optimization technique.

17. The method of claim 16 wherein the numerical, constrained optimization technique is a weighted least-squared numerical optimization.

18. The method of claim 16 wherein the injection procedure input is optimized to minimize a mass of a contrast enhancing agent in the contrast enhancing fluid delivered to the patient.

19. The method of claim 18 wherein the contrast enhancing agent is iodine, xenon or gadolinium.

20. The method of claim 6 wherein the at least one patient transfer function is determined using a system identification model comprising parameters related to the physiological parameters of the patient.

21. The method of claim 20 wherein the system identification model is discretizable.

22. The method of claim 20 further comprising the steps of:
- (a) developing an initial patient transfer function using estimates of at least one of the physiological parameters of the patient;
- (b) performing an injection; and
- (c) revising the patient transfer function based upon at least one time enhancement output of the injection.

23. The method of claim 22 wherein the at least one patient physiological parameter is measured from the at least one time enhancement output.

24. The method of claim 22 wherein the injection is a test injection performed prior to a diagnostic imaging procedure.

25. The method of claim 24 wherein time enhancement outputs resulting from the test injection are measured for at least two different regions of interest.

26. The method of claim 25 wherein a first time enhancement output is measured in an ascending aorta or a descending aorta and a second time enhancement output is measured in a pulmonary artery trunk.

27. The method of claim 25 wherein differences between the time enhancement outputs provide a measure of at least one patient physiological parameter.

28. The method of claim 27 wherein a first time enhancement output is measured in an ascending aorta or a descending aorta and a second time enhancement output is measured in a pulmonary artery trunk.

29. The method of claim 28 wherein the at least one patient physiological parameter is cardiac output, blood volume in a region, a rate transfer term or a transit delay.

30. The method of claim 27 wherein the at least one patient physiological parameter is a parameter of the cardiopulmonary system.

31. The method of claim 30 wherein the at least one patient physiological parameter is cardiac output, blood volume in a region, a rate transfer term or a transit delay.

32. The method of claim 20 wherein the at least one patient transfer function is updated with data collected during an imaging injection.

33. The method of claim 6 wherein the at least one patient transfer function is determined at least in part on the basis of at least one injection.

34. The method of claim 33 wherein the at least one injection is a test injection performed prior to a diagnostic imaging procedure.

35. The method of claim 34 wherein more than one test injection is performed.

36. The method of claim 35 where one test injection comprises injection of a contrast medium only and another test injection comprises injection of a contrast medium followed by injection of a non-contrast fluid.

37. The method of claim 34 wherein the test injection comprises injection of a contrast medium followed by injection of a non-contrast fluid.

38. The method of claim 37 wherein the non-contrast fluid is injected at substantially the same volumetric flow rate as a flow rate of the contrast medium preceding the injection of the non-contrast fluid.

39. The method of claim 38 wherein the non-contrast fluid is saline.

40. An injector system for the delivery of a fluid to a patient comprising:

(a) an injector; and (b) a controller in communicative connection with the injector, the controller comprising:

(I) at least one patient transfer function determined for the patient based upon data specific to the patient, the at least one patient transfer function providing a time enhancement output for a given input, the data specific to the patient including at least one of an estimate of physiologic parameters of the patient, an estimate of anatomic parameters of the patient and an enhancement caused by an injection of the fluid into the patient; and (II) a processor to determine an injection procedure input for a desired time enhancement output using the at least one patient transfer function.

41. The injector system of claim 40 wherein the injection procedure input is determined considering at least one operational limitation or constraint of the injector.

42. The injector system of claim 40 wherein the injection procedure input is determined using an analytical solution or a numerical, constrained optimization technique.

43. The injector system of claim 42 wherein the numerical, constrained optimization technique is a weighted least-squared numerical optimization.

44. The injector system of claim 42 wherein the injection procedure input is optimized to minimize a mass of a contrast enhancing agent in the fluid delivered to the patient.

45. The injector system of claim 44 wherein the contrast enhancing agent is iodine, xenon or gadolinium.

46. The injector system of claim 40 wherein the fluid is a CT contrast enhancing fluid, a MRI contrast enhancing fluid, an ultrasound enhancing imaging fluid or a radioactive contrast enhancing fluid.

47. A method of controlling an injector in a medical imaging procedure, comprising:

(a) determining at least one mathematical model to predict a time enhancement response resulting from an injection of a contrast medium;

(b) determining an injection protocol to approximate a predetermined time enhancement response in a patient by determining a constrained input solution to the at least one mathematical model; and (c) using the injection protocol to control the injector during the medical imaging procedure to control the injection of the contrast medium into the patient to create an image of a region of interest.

48. The method of claim 47 further comprising the step of changing the injection protocol as a result of feedback regarding the time enhancement response during the imaging procedure.

49. The method of claim 47 further comprising the step of changing the injection protocol as a result of data regarding at least one patient physiological parameter during the imaging procedure.

50. The method of claim 47 wherein the step of determining an injection protocol to approximate the predetermined time enhancement response is accomplished using a numerical solver or a numerical optimizer.

51. The method of claim 47 wherein the constrained input solution to the mathematical model is constrained by at least one operational limitation of the injector.

52. The method of claim 47 wherein the constrained input solution to the mathematical model is constrained by at least one operational limitation related to patient safety or comfort.

53. The method of claim 47 wherein the injection of the contrast medium is commenced at one time and an image scan of the region of interest is commenced at a second time determined at least in part on the basis of the mathematical model.

54. The method of claim 53 wherein the second time is determined on the basis of a prediction of a time of attainment of a predetermined enhancement level as determined by the mathematical model.

55. The method of claim 47 wherein the at least one mathematical model is a patient transfer function for the patient based upon data specific to the patient, the at least one patient transfer function providing a time enhancement output for a given input.

56. The method of claim 55 wherein the patient transfer function is determined using a system identification model comprising parameters related to physiological parameters of the patient or is determined using a mathematic identification model determined by collecting data corresponding to a time enhancement curve resulting from the injection of the patient, wherein the mathematical identification model describes the data.

57. A method of controlling injection of a pharmaceutical fluid into a patient using an injector having a controller in communicative connection with a computer memory in a medical procedure, comprising:

(a) collecting data corresponding to a patient response curve resulting from an injection of the pharmaceutical fluid;

(b) choosing at least one mathematical model from a plurality of mathematical models stored in the computer memory to describe the data;

(c) adapting the at least one mathematical model to the collected data; and (d) controlling the injector via the controller during the medical procedure to control the injection of the pharmaceutical fluid into the patient to create a patient response at least in part on the basis of the at least one mathematical model.

58. An imaging system, comprising:

(a) an imager to create an image of a region of interest of a patient;

(b) an injector adapted to inject a contrast medium; and (c) a controller in operative communication with the injector to control the injector, the controller comprising:

(I) at least one patient transfer function determined for the patient based upon data specific to the patient, the at least one patient transfer function providing a time enhancement output for a given input, the data specific to the patient including at least one of an estimate of physiologic parameters of the patient, an estimate of anatomic parameters of the patient and an enhancement caused by an injection of the contrast medium into the patient; and (II) a processor to determine an injection procedure input for a desired time enhancement output using the at least one patient transfer function.

* * * * *

UNITED STATES PATENT AND TRADEMARK OFFICE

CERTIFICATE OF CORRECTION

PATENT NO. : 8,295,914 B2
APPLICATION NO. : 11/575846
DATED : October 23, 2012
INVENTOR(S) : Kalafut et al.

It is certified that error appears in the above-identified patent and that said Letters Patent is hereby corrected as shown below:

On the Title Page, item (56), under “OTHER PUBLICATIONS”, Lines 1-4, delete “Cademartiri, F and Luccichenti, ................ 16.”.

On Title Page 3, item (56), under “OTHER PUBLICATIONS”, Column 1, Line 10, delete “Manual”,” and insert -- Manual”, Document Number 600950, --, therefor.

On Title Page 3, item (56), under “OTHER PUBLICATIONS”, Column 1, Line 13, delete “Radio!.” and insert -- Radiol. --, therefor.

On Title Page 3, item (56), under “OTHER PUBLICATIONS”, Column 1, Line 19, delete “F” and insert -- F. --, therefor.

On Title Page 3, item (56), under “OTHER PUBLICATIONS”, Column 2, Lines 11-14, delete “D. Fleischmann and K. Hittmair, ................ 1999.”.

On Title Page 3, item (56), under “OTHER PUBLICATIONS”, Column 2, Line 16, delete “Dyanamics”,” and insert -- Dynamics”, --, therefor.

On Title Page 3, item (56), under “OTHER PUBLICATIONS”, Column 2, Line 32, delete “289-2999,” and insert -- 289-299. --, therefor.

On Title Page 3, item (56), under “OTHER PUBLICATIONS”, Column 2, Lines 33-34, delete “Guytan, A.C., ................ ISBN:07216436004.”.

On Title Page 3, item (56), under “OTHER PUBLICATIONS”, Column 2, Line 36, delete “D,” and insert -- D., --, therefor.

Signed and Sealed this
Twenty-ninth Day of October, 2013

Teresa Stanek Rea
*Deputy Director of the United States Patent and Trademark Office*

IN THE DRAWINGS

In Fig, 14, Sheet 11 of 17, delete “Emperical” and insert -- Empirical --, therefor.

In Fig. 19B, Sheet 17 of 17, delete “Expected Scan Duration Desired Enhancement Leve” and insert -- Expected Scan Duration Desired Enhancement Level --, therefor.

IN THE SPECIFICATION

In Column 6, Line 52, delete “mathematic” and insert -- mathematical --, therefor.

In Column 8, Line 57, delete “a” and insert -- an --, therefor.

In Column 9, Line 44, delete “mathematic” and insert -- mathematical --, therefor.

In Column 12, Line 50, delete “(i.e.” and insert -- (i.e., --, therefor.

In Column 13, Line 63, delete “may” and insert -- many --, therefor.

In Column 17, Line 13, delete “al” and insert -- al. --, therefor.

In Column 17, Line 25, in Equation (8), delete “PeakEhn[HU]” and insert -- PeakEnh[HU] --, therefor.

In Column 18, Line 18, delete “ehancement” and insert -- enhancement --, therefor.

In Column 20, Line 46, delete “Mathworks,” and insert -- MathWorks, --, therefor.

In Column 25, Line 10, delete “of” and insert -- of an --, therefor.

In Column 25, Line 20, delete “Once” and insert -- One --, therefor.

In Columns 25-26, Lines 49-67 & 1-12, delete “It is desirable that the image .............. of an imaging injection.”.

In Column 26, Line 12, below “imaging injection.”, insert as a new paragraph -- Even if the precision is improved as described above, there can still be noise in the Hounsfield units calculation due to the statistical absorption of the X-rays. Using as large as possible a region of interest reduces or minimizes this effect. The high frequency variations or noise will tend to be averaged out. More sophisticated area computation approaches can be applied as well. Another approach is to fit a curve to the measured value of Hounsfield units versus time. One curve commonly used is the gamma variate curve. A polynomial curve could also be used. This smoothes out the noise and provides estimations of enhancement values at times between the actual measurements. The measured curves of Figures 16A through 17B indicate the average of the ROI (region of interest) in the vessel, plus one standard deviation and minus one standard deviation. --, therefor.

IN THE SPECIFICATION

In Column 27, Line 14, delete “application,” and insert -- application --, therefor.

IN THE CLAIMS

In Column 31, Line 9, in Claim 27, delete “of” and insert -- of the --, therefor.

In Column 32, Line 66, in Claim 56, delete “mathematic” and insert -- mathematical --, therefor.

UNITED STATES PATENT AND TRADEMARK OFFICE

CERTIFICATE OF CORRECTION

PATENT NO. : 8,295,914 B2
APPLICATION NO. : 11/575846
DATED : October 23, 2012
INVENTOR(S) : John F. Kalafut It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1422 days.

Signed and Sealed this
Eighth Day of July, 2014

Michelle K. Lee
*Deputy Director of the United States Patent and Trademark Office*